US008241293B2

(12) United States Patent
Stone et al.

(10) Patent No.: US 8,241,293 B2
(45) Date of Patent: Aug. 14, 2012

(54) PATIENT SPECIFIC HIGH TIBIA OSTEOTOMY

(75) Inventors: Kevin T. Stone, Winona Lake, IN (US); Robert Metzger, Wakarusa, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 220 days.

(21) Appl. No.: 12/714,023

(22) Filed: Feb. 26, 2010

(65) Prior Publication Data

US 2010/0152782 A1 Jun. 17, 2010

Related U.S. Application Data

(63) Continuation-in-part of application No. 12/571,969, filed on Oct. 1, 2009, which is a continuation-in-part of application No. 12/389,901, filed on Sep. 20, 2009, now Pat. No. 8,133,234, which is a continuation-in-part of application No. 12/211,407, filed on Sep. 16, 2008, which is a continuation-in-part of application No. 12/039,849, filed on Feb. 29, 2008, and a continuation-in-part of application No. 11/756,057, filed on May 31, 2007, now Pat. No. 8,092,465, which is a continuation-in-part of application No. 11/971,390, filed on Jan. 9, 2008, now Pat. No. 8,070,752, which is a continuation-in-part of application No. 11/363,548, filed on Feb. 27, 2006, now Pat. No. 7,780,672, which is a continuation-in-part of application No. 12/025,414, filed on Feb. 4, 2008, which is a continuation-in-part of application No. 12/103,834, filed on Apr. 16, 2008, now Pat. No. 7,967,868, which is a continuation-in-part of application No. 12/483,807, filed on Jun. 12, 2009, which is a continuation-in-part of application No. 12/371,096, filed on Feb. 13, 2009, which is a continuation-in-part of application No. 12/103,824, filed on Apr. 16, 2008.

(60) Provisional application No. 60/953,620, filed on Aug. 2, 2007, provisional application No. 60/947,813, filed on Jul. 3, 2007, provisional application No. 60/911,297, filed on Apr. 12, 2007, provisional application No. 60/892,349, filed on Mar. 1, 2007, provisional application No. 60/812,694, filed on Jun. 9, 2006, provisional application No. 60/953,637, filed on Aug. 2, 2007, provisional application No. 60/912,178, filed on Apr. 17, 2007, provisional application No. 60/912,178, filed on Apr. 17, 2007.

(51) Int. Cl.
*A61F 5/00* (2006.01)
*A61F 2/38* (2006.01)

(52) U.S. Cl. ...................................... 606/87; 623/20.32

(58) Field of Classification Search ............... 623/20.32, 623/20.14, 18.11, 16.11; 606/53, 247, 248, 606/300, 79, 87, 88, 86 R, 84, 99, 60, 286
See application file for complete search history.

(56) References Cited

U.S. PATENT DOCUMENTS 1,480,285 A 1/1924 Moore
(Continued)

FOREIGN PATENT DOCUMENTS

CA 2447694 A1 12/2002
(Continued)

OTHER PUBLICATIONS

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

(Continued)

*Primary Examiner* — Alvin J Stewart
(74) *Attorney, Agent, or Firm* — Harness, Dickey

(57) ABSTRACT

A surgical kit includes a patient-specific alignment guide having a three-dimensional engagement surface custom-made by computer imaging to conform to a corresponding portion of a patient's tibial bone. The patient-specific alignment guide defines an elongated planar slot for guiding a blade. The planar slot is oriented at a selected angle and at a selected position relative to an anatomic axis of the patient when the engagement surface engages the corresponding portion of the tibial bone. The selected angle and selected position are determined during a pre-operative planning stage.

20 Claims, 9 Drawing Sheets

U.S. PATENT DOCUMENTS

| | | | |
|---|---|---|---|
| 2,181,746 A | 11/1939 | Siebrandt | |
| 2,407,845 A | 9/1946 | Nemeyer | |
| 2,618,913 A | 11/1952 | Plancon et al. | |
| 2,910,978 A | 11/1959 | Urist | |
| 3,840,904 A | 10/1974 | Tronzo | |
| 4,246,895 A | 1/1981 | Rehder | |
| 4,306,866 A | 12/1981 | Weissman | |
| 4,324,006 A | 4/1982 | Charnley | |
| 4,421,112 A * | 12/1983 | Mains et al. | 606/88 |
| 4,436,684 A | 3/1984 | White | |
| 4,475,549 A | 10/1984 | Oh | |
| 4,506,393 A | 3/1985 | Murphy | |
| 4,524,766 A | 6/1985 | Petersen | |
| 4,619,658 A | 10/1986 | Pappas et al. | |
| 4,621,630 A | 11/1986 | Kenna | |
| 4,632,111 A | 12/1986 | Roche | |
| 4,633,862 A | 1/1987 | Petersen | |
| 4,663,720 A | 5/1987 | Duret et al. | |
| 4,695,283 A | 9/1987 | Aldinger | |
| 4,696,292 A | 9/1987 | Heiple | |
| 4,703,751 A * | 11/1987 | Pohl | 606/62 |
| 4,704,686 A | 11/1987 | Aldinger | |
| 4,721,104 A | 1/1988 | Kaufman et al. | |
| 4,778,474 A | 10/1988 | Homsy | |
| 4,800,874 A | 1/1989 | David et al. | |
| 4,821,213 A | 4/1989 | Cline et al. | |
| 4,822,365 A | 4/1989 | Walker et al. | |
| 4,841,975 A | 6/1989 | Woolson | |
| 4,846,161 A | 7/1989 | Roger | |
| 4,871,975 A | 10/1989 | Nawata et al. | |
| 4,893,619 A | 1/1990 | Dale et al. | |
| 4,896,663 A | 1/1990 | Vandewalls | |
| 4,927,422 A | 5/1990 | Engelhardt | |
| 4,936,862 A | 6/1990 | Walker et al. | |
| 4,952,213 A * | 8/1990 | Bowman et al. | 606/79 |
| 4,959,066 A | 9/1990 | Dunn et al. | |
| 4,976,737 A | 12/1990 | Leake | |
| 4,979,949 A | 12/1990 | Matsen, III et al. | |
| 4,985,037 A | 1/1991 | Petersen | |
| 5,002,579 A | 3/1991 | Copf et al. | |
| 5,007,936 A | 4/1991 | Woolson | |
| 5,030,221 A | 7/1991 | Buechel et al. | |
| 5,041,117 A | 8/1991 | Engelhardt | |
| 5,053,039 A * | 10/1991 | Hofmann et al. | 606/87 |
| 5,086,401 A | 2/1992 | Glassman et al. | |
| 5,098,383 A | 3/1992 | Hemmy et al. | |
| 5,098,436 A | 3/1992 | Ferrante et al. | |
| 5,108,425 A | 4/1992 | Hwang | |
| 5,122,144 A * | 6/1992 | Bert et al. | 606/88 |
| 5,129,908 A | 7/1992 | Petersen | |
| 5,129,909 A * | 7/1992 | Sutherland | 606/88 |
| 5,133,760 A | 7/1992 | Petersen et al. | |
| 5,140,777 A | 8/1992 | Ushiyama et al. | |
| 5,150,304 A | 9/1992 | Berchem et al. | |
| 5,176,684 A | 1/1993 | Ferrante et al. | |
| 5,246,444 A * | 9/1993 | Schreiber | 606/87 |
| 5,258,032 A | 11/1993 | Bertin | |
| 5,261,915 A | 11/1993 | Durlacher et al. | |
| 5,274,565 A | 12/1993 | Reuben | |
| 5,299,288 A | 3/1994 | Glassman et al. | |
| 5,300,077 A | 4/1994 | Howell | |
| 5,320,625 A | 6/1994 | Bertin | |
| 5,342,366 A | 8/1994 | Whiteside et al. | |
| 5,344,423 A | 9/1994 | Dietz et al. | |
| 5,360,446 A | 11/1994 | Kennedy | |
| 5,368,858 A | 11/1994 | Hunziker | |
| 5,370,692 A | 12/1994 | Fink et al. | |
| 5,370,699 A | 12/1994 | Hood et al. | |
| 5,405,395 A | 4/1995 | Coates | |
| 5,408,409 A | 4/1995 | Glassman et al. | |
| 5,415,662 A * | 5/1995 | Ferrante et al. | 606/86 R |
| 5,438,263 A | 8/1995 | Dworkin et al. | |
| 5,440,496 A | 8/1995 | Andersson et al. | |
| 5,448,489 A | 9/1995 | Reuben | |
| 5,449,360 A * | 9/1995 | Schreiber | 606/87 |
| 5,452,407 A | 9/1995 | Crook | |
| 5,454,816 A | 10/1995 | Ashby | |
| 5,472,415 A * | 12/1995 | King et al. | 606/102 |
| 5,474,559 A | 12/1995 | Bertin et al. | |
| 5,490,854 A * | 2/1996 | Fisher et al. | 606/88 |
| 5,496,324 A | 3/1996 | Barnes | |
| 5,507,833 A | 4/1996 | Bohn | |
| 5,514,519 A | 5/1996 | Neckers | |
| 5,520,695 A | 5/1996 | Luckman | |
| 5,527,317 A * | 6/1996 | Ashby et al. | 606/91 |
| 5,539,649 A | 7/1996 | Walsh et al. | |
| 5,540,695 A * | 7/1996 | Levy | 606/87 |
| 5,554,190 A | 9/1996 | Draenert | |
| 5,560,096 A | 10/1996 | Stephens | |
| 5,571,110 A | 11/1996 | Matsen, III et al. | |
| 5,578,037 A | 11/1996 | Sanders et al. | |
| 5,595,703 A | 1/1997 | Swaelens et al. | |
| 5,607,431 A | 3/1997 | Dudasik et al. | |
| 5,613,969 A * | 3/1997 | Jenkins, Jr. | 606/87 |
| 5,620,448 A * | 4/1997 | Puddu | 606/87 |
| 5,634,927 A | 6/1997 | Houston et al. | |
| 5,658,294 A | 8/1997 | Sederholm | |
| 5,662,656 A * | 9/1997 | White | 606/88 |
| 5,677,107 A | 10/1997 | Neckers | |
| 5,681,354 A | 10/1997 | Eckhoff | |
| 5,682,886 A | 11/1997 | Delp et al. | |
| 5,690,635 A | 11/1997 | Matsen, III et al. | |
| 5,702,460 A | 12/1997 | Carls et al. | |
| 5,704,941 A | 1/1998 | Jacober et al. | |
| 5,722,978 A * | 3/1998 | Jenkins, Jr. | 606/87 |
| 5,725,376 A | 3/1998 | Poirier | |
| 5,725,593 A | 3/1998 | Caracciolo | |
| 5,735,277 A | 4/1998 | Schuster | |
| 5,748,767 A | 5/1998 | Raab | |
| 5,749,875 A * | 5/1998 | Puddu | 606/87 |
| 5,749,876 A | 5/1998 | Duvillier et al. | |
| 5,762,125 A | 6/1998 | Mastrorio | |
| 5,768,134 A * | 6/1998 | Swaelens et al. | 700/121 |
| 5,769,092 A | 6/1998 | Williamson, Jr. | |
| 5,786,217 A | 7/1998 | Tubo et al. | |
| 5,792,143 A | 8/1998 | Samuelson et al. | |
| 5,798,924 A * | 8/1998 | Eufinger et al. | 700/117 |
| 5,799,055 A | 8/1998 | Peshkin et al. | |
| 5,860,981 A | 1/1999 | Bertin et al. | |
| 5,871,018 A | 2/1999 | Delp et al. | |
| 5,876,456 A | 3/1999 | Sederholm et al. | |
| 5,879,398 A | 3/1999 | Swarts et al. | |
| 5,879,402 A | 3/1999 | Lawes et al. | |
| 5,880,976 A | 3/1999 | DiGioia III et al. | |
| 5,885,297 A | 3/1999 | Matsen, III | |
| 5,885,298 A | 3/1999 | Herrington et al. | |
| 5,895,389 A | 4/1999 | Schenk et al. | |
| 5,899,907 A | 5/1999 | Johnson | |
| 5,901,060 A | 5/1999 | Schall et al. | |
| 5,911,724 A | 6/1999 | Wehrli | |
| 5,925,049 A * | 7/1999 | Gustilo et al. | 606/82 |
| 5,942,370 A | 8/1999 | Neckers | |
| 5,967,777 A | 10/1999 | Klein et al. | |
| 5,976,149 A | 11/1999 | Masini | |
| 5,980,526 A * | 11/1999 | Johnson et al. | 606/86 R |
| 6,033,415 A | 3/2000 | Mittelstadt et al. | |
| 6,059,833 A | 5/2000 | Doets | |
| 6,086,593 A * | 7/2000 | Bonutti | 606/87 |
| 6,120,510 A | 9/2000 | Albrektsson et al. | |
| 6,120,544 A | 9/2000 | Grundei et al. | |
| 6,126,690 A | 10/2000 | Ateshian et al. | |
| 6,136,033 A | 10/2000 | Suemer | |
| 6,156,069 A | 12/2000 | Amstutz | |
| 6,161,080 A | 12/2000 | Aouni-Ateshian et al. | |
| 6,187,010 B1 | 2/2001 | Masini | |
| 6,195,615 B1 | 2/2001 | Lysen | |
| 6,203,546 B1 * | 3/2001 | MacMahon | 606/87 |
| 6,205,411 B1 | 3/2001 | DiGioia, III et al. | |
| 6,206,927 B1 | 3/2001 | Fell et al. | |
| 6,254,604 B1 | 7/2001 | Howell | |
| 6,258,097 B1 | 7/2001 | Cook et al. | |
| 6,264,698 B1 * | 7/2001 | Lawes et al. | 623/22.12 |
| 6,273,891 B1 | 8/2001 | Masini | |
| 6,290,727 B1 | 9/2001 | Otto et al. | |
| 6,293,971 B1 | 9/2001 | Nelson et al. | |
| 6,312,473 B1 | 11/2001 | Oshida | |
| 6,319,285 B1 | 11/2001 | Chamier et al. | |

| | | |
|---|---|---|
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |
| 6,395,005 B1 | 5/2002 | Lovell |
| 6,427,698 B1 * | 8/2002 | Yoon .............................. 128/898 |
| 6,459,948 B1 | 10/2002 | Ateshian et al. |
| 6,463,351 B1 | 10/2002 | Clynch |
| 6,475,243 B1 | 11/2002 | Sheldon et al. |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 * | 3/2003 | Brosseau et al. ............... 600/595 |
| 6,547,823 B2 * | 4/2003 | Scarborough et al. ...... 623/17.16 |
| 6,554,837 B1 | 4/2003 | Hauri et al. |
| 6,556,008 B2 * | 4/2003 | Thesen .......................... 324/307 |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 * | 6/2003 | Robie et al. ...................... 606/88 |
| 6,575,982 B1 * | 6/2003 | Bonutti ............................ 606/90 |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzle III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 * | 3/2004 | Krause et al. .................. 600/427 |
| 6,712,856 B1 * | 3/2004 | Carignan et al. ........... 623/20.35 |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 * | 11/2004 | Schmieding .................. 128/898 |
| 6,827,723 B2 | 12/2004 | Carson |
| 6,887,247 B1 | 5/2005 | Couture et al. |
| 6,905,514 B2 * | 6/2005 | Carignan et al. ........... 623/20.35 |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 * | 6/2008 | Moctezuma de La Barrera ........................ 600/427 |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,517,365 B2 * | 4/2009 | Carignan et al. ........... 623/20.35 |
| 7,527,631 B2 | 5/2009 | Maroney et al. |
| 7,534,263 B2 * | 5/2009 | Burdulis et al. ............ 623/14.12 |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 * | 5/2010 | Ringeisen et al. ............... 521/50 |
| 7,780,740 B2 * | 8/2010 | Steinberg ................... 623/22.21 |
| 7,794,466 B2 * | 9/2010 | Merchant et al. ................ 606/87 |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 * | 2/2011 | Borden et al. ............. 623/23.76 |
| 7,892,261 B2 * | 2/2011 | Bonutti .......................... 606/279 |
| 7,896,921 B2 | 3/2011 | Smith et al. |
| 7,935,119 B2 * | 5/2011 | Ammann et al. ................ 606/87 |
| 7,935,150 B2 * | 5/2011 | Carignan et al. ........... 623/20.35 |
| 7,938,861 B2 | 5/2011 | King et al. |
| 7,959,637 B2 * | 6/2011 | Fox et al. ......................... 606/88 |
| 7,962,196 B2 | 6/2011 | Tuma |
| 7,963,968 B2 | 6/2011 | Dees, Jr. |
| 7,967,823 B2 * | 6/2011 | Ammann et al. ................ 606/88 |
| 7,967,868 B2 * | 6/2011 | White et al. ................ 623/20.35 |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 * | 11/2011 | Ammann et al. ................ 606/87 |
| 8,070,752 B2 * | 12/2011 | Metzger et al. .................. 606/88 |
| 8,083,745 B2 * | 12/2011 | Lang et al. ...................... 606/87 |
| 8,083,746 B2 * | 12/2011 | Novak .............................. 606/88 |
| 8,083,749 B2 * | 12/2011 | Taber ............................... 606/96 |
| 8,086,336 B2 * | 12/2011 | Christensen .................... 700/98 |
| 8,092,465 B2 * | 1/2012 | Metzger et al. .................. 606/96 |
| 8,133,230 B2 * | 3/2012 | Stevens et al. ................... 606/87 |
| 8,137,406 B2 * | 3/2012 | Novak et al. ............... 623/20.32 |
| 2001/0005797 A1 | 6/2001 | Barlow et al. |
| 2001/0011190 A1 | 8/2001 | Park |
| 2001/0054478 A1 | 12/2001 | Watanabe et al. |

| | | |
|---|---|---|
| 2002/0007294 A1 | 1/2002 | Bradbury et al. |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1* | 3/2003 | Lang et al. ............... 623/16.11 |
| 2003/0105526 A1* | 6/2003 | Bryant et al. ............... 623/16.11 |
| 2003/0109784 A1* | 6/2003 | Loh et al. ............... 600/427 |
| 2003/0120276 A1 | 6/2003 | Tallarida et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1* | 7/2004 | Bonutti ............... 623/16.11 |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2005/0008887 A1 | 1/2005 | Haymann et al. |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1* | 4/2005 | Singhatat et al. ............... 606/86 |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0171545 A1 | 8/2005 | Walsh et al. |
| 2005/0177245 A1* | 8/2005 | Leatherbury et al. ......... 623/23.5 |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0234461 A1 | 10/2005 | Burdulis et al. |
| 2005/0234468 A1 | 10/2005 | Carson |
| 2005/0240267 A1* | 10/2005 | Randall et al. ............... 623/17.11 |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1* | 11/2005 | Novak ............... 606/87 |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1* | 12/2005 | Novak ............... 606/88 |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0190086 A1 | 8/2006 | Clemow et al. |
| 2006/0195198 A1 | 8/2006 | James |
| 2006/0204932 A1 | 9/2006 | Haymann et al. |
| 2006/0210644 A1 | 9/2006 | Levin |
| 2006/0217808 A1* | 9/2006 | Novak et al. ............... 623/17.11 |
| 2006/0235421 A1 | 10/2006 | Rosa et al. |
| 2006/0271058 A1 | 11/2006 | Ashton et al. |
| 2006/0276796 A1* | 12/2006 | Creger et al. ............... 606/79 |
| 2006/0276797 A1 | 12/2006 | Botimer |
| 2006/0287733 A1 | 12/2006 | Bonutti |
| 2007/0015995 A1 | 1/2007 | Lang et al. |
| 2007/0016209 A1* | 1/2007 | Ammann et al. ............... 606/79 |
| 2007/0027680 A1 | 2/2007 | Ashley et al. |
| 2007/0066917 A1 | 3/2007 | Hodorek et al. |
| 2007/0073137 A1 | 3/2007 | Schoenefeld |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100450 A1 | 5/2007 | Hodorek |
| 2007/0100462 A1 | 5/2007 | Lang et al. |
| 2007/0118055 A1 | 5/2007 | McCombs |
| 2007/0118243 A1 | 5/2007 | Schroeder et al. |
| 2007/0150068 A1 | 6/2007 | Dong et al. |
| 2007/0156066 A1 | 7/2007 | McGinley et al. |
| 2007/0156171 A1* | 7/2007 | Lang et al. ............... 606/205 |
| 2007/0162038 A1 | 7/2007 | Tuke |
| 2007/0162039 A1 | 7/2007 | Wozencroft |
| 2007/0173946 A1 | 7/2007 | Bonutti |
| 2007/0173948 A1 | 7/2007 | Meridew et al. |
| 2007/0185498 A2 | 8/2007 | Lavallee |
| 2007/0191962 A1 | 8/2007 | Jones et al. |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0219639 A1 | 9/2007 | Otto et al. |
| 2007/0219640 A1 | 9/2007 | Steinberg |
| 2007/0224238 A1 | 9/2007 | Mansmann et al. |
| 2007/0226986 A1 | 10/2007 | Park et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |

| | | | |
|---|---|---|---|
| 2007/0233272 A1 | 10/2007 | Boyce et al. | |
| 2007/0238069 A1 | 10/2007 | Lovald et al. | |
| 2007/0239282 A1 | 10/2007 | Caylor et al. | |
| 2007/0239481 A1 | 10/2007 | DiSilvestro et al. | |
| 2007/0250169 A1 | 10/2007 | Lang | |
| 2007/0253617 A1 | 11/2007 | Arata et al. | |
| 2007/0255288 A1 | 11/2007 | Mahfouz et al. | |
| 2007/0255412 A1 | 11/2007 | Hajaj et al. | |
| 2007/0262867 A1 | 11/2007 | Westrick et al. | |
| 2007/0272747 A1 | 11/2007 | Woods et al. | |
| 2007/0276224 A1 | 11/2007 | Lang et al. | |
| 2007/0276400 A1 | 11/2007 | Moore et al. | |
| 2007/0276501 A1 | 11/2007 | Betz et al. | |
| 2007/0288030 A1 | 12/2007 | Metzger et al. | |
| 2008/0009952 A1 | 1/2008 | Hodge | |
| 2008/0015604 A1* | 1/2008 | Collazo | 606/87 |
| 2008/0015605 A1* | 1/2008 | Collazo | |
| 2008/0021299 A1 | 1/2008 | Meulink | |
| 2008/0021494 A1 | 1/2008 | Schmelzeisen-Redeker et al. | |
| 2008/0021567 A1 | 1/2008 | Meulink et al. | |
| 2008/0027563 A1 | 1/2008 | Johnson et al. | |
| 2008/0033442 A1 | 2/2008 | Amiot et al. | |
| 2008/0051799 A1* | 2/2008 | Bonutti | 606/87 |
| 2008/0051910 A1 | 2/2008 | Kammerzell et al. | |
| 2008/0058945 A1 | 3/2008 | Hajaj et al. | |
| 2008/0058947 A1 | 3/2008 | Earl et al. | |
| 2008/0062183 A1 | 3/2008 | Swaelens | |
| 2008/0065225 A1 | 3/2008 | Wasielewski et al. | |
| 2008/0112996 A1 | 5/2008 | Harlow et al. | |
| 2008/0114370 A1 | 5/2008 | Schoenefeld | |
| 2008/0133022 A1 | 6/2008 | Caylor | |
| 2008/0140209 A1 | 6/2008 | Iannotti et al. | |
| 2008/0140213 A1* | 6/2008 | Ammann et al. | 623/20.32 |
| 2008/0146969 A1 | 6/2008 | Kurtz | |
| 2008/0147072 A1 | 6/2008 | Park et al. | |
| 2008/0161815 A1 | 7/2008 | Schoenefeld et al. | |
| 2008/0172125 A1 | 7/2008 | Ek | |
| 2008/0195099 A1 | 8/2008 | Minas | |
| 2008/0195107 A1 | 8/2008 | Cuckler et al. | |
| 2008/0195216 A1 | 8/2008 | Philipp | |
| 2008/0200926 A1 | 8/2008 | Verard et al. | |
| 2008/0208200 A1 | 8/2008 | Crofford | |
| 2008/0208353 A1 | 8/2008 | Kumar et al. | |
| 2008/0215059 A1 | 9/2008 | Carignan et al. | |
| 2008/0230422 A1 | 9/2008 | Pleil et al. | |
| 2008/0234664 A1 | 9/2008 | May et al. | |
| 2008/0234683 A1 | 9/2008 | May | |
| 2008/0234685 A1 | 9/2008 | Gjerde | |
| 2008/0234833 A1 | 9/2008 | Bandoh et al. | |
| 2008/0243127 A1 | 10/2008 | Lang et al. | |
| 2008/0255674 A1 | 10/2008 | Rahaman et al. | |
| 2008/0257363 A1 | 10/2008 | Schoenefeld et al. | |
| 2008/0262500 A1 | 10/2008 | Collazo | |
| 2008/0262624 A1 | 10/2008 | White et al. | |
| 2008/0269906 A1 | 10/2008 | Iannotti et al. | |
| 2008/0275452 A1 | 11/2008 | Lang et al. | |
| 2008/0281328 A1 | 11/2008 | Lang et al. | |
| 2008/0281329 A1 | 11/2008 | Fitz et al. | |
| 2008/0281426 A1 | 11/2008 | Fitz et al. | |
| 2008/0287954 A1* | 11/2008 | Kunz et al. | 606/87 |
| 2008/0294266 A1 | 11/2008 | Steinberg | |
| 2008/0300600 A1 | 12/2008 | Guelat et al. | |
| 2008/0306558 A1 | 12/2008 | Hakki | |
| 2008/0312659 A1* | 12/2008 | Metzger et al. | 606/87 |
| 2008/0319448 A1 | 12/2008 | Lavallee et al. | |
| 2009/0012526 A1 | 1/2009 | Fletcher | |
| 2009/0018546 A1 | 1/2009 | Daley | |
| 2009/0018666 A1 | 1/2009 | Grundei et al. | |
| 2009/0024131 A1 | 1/2009 | Metzger et al. | |
| 2009/0043556 A1 | 2/2009 | Axelson et al. | |
| 2009/0076371 A1 | 3/2009 | Lang et al. | |
| 2009/0076512 A1 | 3/2009 | Ammann et al. | |
| 2009/0082770 A1 | 3/2009 | Worner et al. | |
| 2009/0087276 A1 | 4/2009 | Rose | |
| 2009/0088674 A1 | 4/2009 | Caillouette et al. | |
| 2009/0088753 A1 | 4/2009 | Aram et al. | |
| 2009/0088754 A1 | 4/2009 | Aker et al. | |
| 2009/0088755 A1 | 4/2009 | Aker et al. | |
| 2009/0088758 A1 | 4/2009 | Bennett | |
| 2009/0088759 A1 | 4/2009 | Aram et al. | |
| 2009/0088760 A1 | 4/2009 | Aram et al. | |
| 2009/0088761 A1 | 4/2009 | Roose et al. | |
| 2009/0088763 A1* | 4/2009 | Aram et al. | 606/88 |
| 2009/0088865 A1 | 4/2009 | Brehm | |
| 2009/0088866 A1 | 4/2009 | Case | |
| 2009/0089034 A1 | 4/2009 | Penney et al. | |
| 2009/0089081 A1 | 4/2009 | Haddad | |
| 2009/0093815 A1* | 4/2009 | Fletcher et al. | 606/82 |
| 2009/0093816 A1* | 4/2009 | Roose et al. | 606/87 |
| 2009/0096613 A1 | 4/2009 | Westrick | |
| 2009/0099567 A1* | 4/2009 | Zajac | 606/79 |
| 2009/0105837 A1 | 4/2009 | Lafosse et al. | |
| 2009/0118736 A1 | 5/2009 | Kreuzer | |
| 2009/0131941 A1 | 5/2009 | Park et al. | |
| 2009/0131942 A1* | 5/2009 | Aker et al. | 606/88 |
| 2009/0138020 A1* | 5/2009 | Park et al. | 606/88 |
| 2009/0149965 A1 | 6/2009 | Quaid | |
| 2009/0149977 A1* | 6/2009 | Schendel | 700/98 |
| 2009/0151736 A1 | 6/2009 | Belcher et al. | |
| 2009/0157083 A1* | 6/2009 | Park et al. | 606/88 |
| 2009/0163922 A1* | 6/2009 | Meridew et al. | 606/88 |
| 2009/0163923 A1 | 6/2009 | Flett et al. | |
| 2009/0164024 A1 | 6/2009 | Rudan et al. | |
| 2009/0177282 A1 | 7/2009 | Bureau et al. | |
| 2009/0187193 A1 | 7/2009 | Maroney et al. | |
| 2009/0209884 A1 | 8/2009 | Van Vorhis et al. | |
| 2009/0209961 A1 | 8/2009 | Ferrante et al. | |
| 2009/0222014 A1 | 9/2009 | Bojarski et al. | |
| 2009/0222015 A1* | 9/2009 | Park et al. | 606/89 |
| 2009/0222016 A1* | 9/2009 | Park et al. | 606/89 |
| 2009/0228016 A1 | 9/2009 | Alvarez et al. | |
| 2009/0234360 A1 | 9/2009 | Alexander | |
| 2009/0248044 A1 | 10/2009 | Amiot et al. | |
| 2009/0254093 A1 | 10/2009 | White et al. | |
| 2009/0254367 A1 | 10/2009 | Belcher et al. | |
| 2009/0270868 A1 | 10/2009 | Park et al. | |
| 2009/0274350 A1 | 11/2009 | Pavlovskaia et al. | |
| 2009/0306676 A1* | 12/2009 | Lang et al. | 606/102 |
| 2009/0307893 A1 | 12/2009 | Burdulis, Jr. et al. | |
| 2009/0318836 A1 | 12/2009 | Stone et al. | |
| 2010/0016984 A1 | 1/2010 | Trabish | |
| 2010/0016986 A1 | 1/2010 | Trabish | |
| 2010/0023015 A1* | 1/2010 | Park | 606/87 |
| 2010/0030231 A1* | 2/2010 | Revie et al. | 606/130 |
| 2010/0042105 A1* | 2/2010 | Park et al. | 606/87 |
| 2010/0049195 A1* | 2/2010 | Park et al. | 606/87 |
| 2010/0076439 A1 | 3/2010 | Hatch | |
| 2010/0076505 A1 | 3/2010 | Borja | |
| 2010/0076563 A1 | 3/2010 | Otto et al. | |
| 2010/0076571 A1 | 3/2010 | Hatch | |
| 2010/0082034 A1 | 4/2010 | Remia | |
| 2010/0082035 A1 | 4/2010 | Keefer | |
| 2010/0087829 A1 | 4/2010 | Metzger et al. | |
| 2010/0094295 A1 | 4/2010 | Schnieders et al. | |
| 2010/0105011 A1 | 4/2010 | Karkar et al. | |
| 2010/0121335 A1 | 5/2010 | Penenberg et al. | |
| 2010/0137869 A1 | 6/2010 | Borja et al. | |
| 2010/0137924 A1 | 6/2010 | Tuke et al. | |
| 2010/0145343 A1 | 6/2010 | Johnson et al. | |
| 2010/0145344 A1 | 6/2010 | Jordan et al. | |
| 2010/0152782 A1* | 6/2010 | Stone et al. | 606/280 |
| 2010/0160917 A1 | 6/2010 | Fitz et al. | |
| 2010/0168754 A1* | 7/2010 | Fitz et al. | 606/88 |
| 2010/0168857 A1 | 7/2010 | Hatch | |
| 2010/0179663 A1* | 7/2010 | Steinberg | 623/22.24 |
| 2010/0185202 A1 | 7/2010 | Lester et al. | |
| 2010/0191244 A1 | 7/2010 | White et al. | |
| 2010/0212138 A1* | 8/2010 | Carroll et al. | 29/446 |
| 2010/0217109 A1 | 8/2010 | Belcher | |
| 2010/0217270 A1 | 8/2010 | Polinski et al. | |
| 2010/0217336 A1 | 8/2010 | Crawford et al. | |
| 2010/0217338 A1* | 8/2010 | Carroll et al. | 606/86 R |
| 2010/0228257 A1 | 9/2010 | Bonutti | |
| 2010/0249657 A1 | 9/2010 | Nycz et al. | |
| 2010/0249796 A1 | 9/2010 | Nycz | |
| 2010/0262150 A1 | 10/2010 | Lian | |
| 2010/0274253 A1 | 10/2010 | Ure | |
| 2010/0281678 A1* | 11/2010 | Burdulis et al. | 29/592 |

| | | | |
|---|---|---|---|
| 2010/0286700 A1* | 11/2010 | Snider et al. ............... 606/89 |
| 2010/0292743 A1* | 11/2010 | Singhal et al. ............ 606/86 R |
| 2010/0305574 A1* | 12/2010 | Fitz et al. .................. 606/88 |
| 2010/0324692 A1* | 12/2010 | Uthgenannt et al. ....... 623/20.35 |
| 2011/0004317 A1 | 1/2011 | Hacking et al. |
| 2011/0015636 A1 | 1/2011 | Katrana et al. |
| 2011/0015639 A1* | 1/2011 | Metzger et al. ............ 606/91 |
| 2011/0015752 A1 | 1/2011 | Meridew |
| 2011/0029091 A1* | 2/2011 | Bojarski et al. ........... 623/20.32 |
| 2011/0029116 A1 | 2/2011 | Jordan et al. |
| 2011/0035012 A1* | 2/2011 | Linares .................... 623/18.11 |
| 2011/0040334 A1* | 2/2011 | Kaes et al. ................ 606/279 |
| 2011/0046735 A1 | 2/2011 | Metzger et al. |
| 2011/0054478 A1 | 3/2011 | Vanasse et al. |
| 2011/0066193 A1* | 3/2011 | Lang et al. ............... 606/86 R |
| 2011/0066245 A1* | 3/2011 | Lang et al. ............... 623/18.11 |
| 2011/0071528 A1 | 3/2011 | Carson |
| 2011/0071529 A1* | 3/2011 | Carson ..................... 606/88 |
| 2011/0071530 A1* | 3/2011 | Carson ..................... 606/88 |
| 2011/0071532 A1 | 3/2011 | Carson |
| 2011/0071533 A1* | 3/2011 | Metzger et al. ............ 606/88 |
| 2011/0092804 A1 | 4/2011 | Schoenefeld et al. |
| 2011/0093086 A1* | 4/2011 | Witt et al. ................. 623/22.15 |
| 2011/0106254 A1* | 5/2011 | Abel et al. ................. 623/16.11 |
| 2011/0125264 A1* | 5/2011 | Bagga et al. ............... 623/16.11 |
| 2011/0151027 A1* | 6/2011 | Clineff et al. ............. 424/722 |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1* | 9/2011 | Maxson et al. ............ 606/88 |
| 2011/0214279 A1* | 9/2011 | Park et al. ................. 29/592 |
| 2011/0218545 A1 | 9/2011 | Catanzarite et al. |
| 2011/0224674 A1 | 9/2011 | White et al. |
| 2011/0257657 A1 | 10/2011 | Turner et al. |
| 2012/0010710 A1* | 1/2012 | Frigg .......................... 623/16.11 |
| 2012/0010711 A1* | 1/2012 | Antonyshyn et al. ...... 623/16.11 |

FOREIGN PATENT DOCUMENTS

| | | |
|---|---|---|
| CA | 2501041 A1 | 4/2004 |
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| EP | 0114505 A1 | 8/1984 |
| EP | 0326768 A2 | 8/1989 |
| EP | 0579868 A2 | 1/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1852072 A2 | 7/2007 |
| EP | 1832239 A1 | 9/2007 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008101090 A2 | 8/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2011018458 A1 | 2/2011 |

OTHER PUBLICATIONS

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

"Patient Matched PMI Implants, C.A.M.R.A. 3-D Imaging," brochure, Biomet, Inc. (1990) 6 pages.

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Chart P., Technical Report: DeVIDE—The Delft Visualisation and Image processing Development Environment, pp. 1-49 (May 31, 2006).
Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.
Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.
Haaker, R.G., et al., "Minimal-invasive naviguert implantierte unikondyläre Knieendoprothese," Orthopäde 2006 35:1073-1079 (2006) Spinger Medizin Verlag.
Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.
Hazan, Eric J., M.D., "Computer-Assisted Orthopaedic Sugery, A New Paradigm," Techniques in Orthopaedics® vol. 18, No. 2, (2003) pp. 221-229.
Hutmacher, Dietmar, W., "Scaffolds in tissue engineering bone and cartilage," Biomaterials, 2000 Elsevier Science Ltd. (pp. 2529-2543).
International Preliminary Report on Patentability for PCT/US2007/013223 issued Nov. 26, 2007.
International Search Report and Written Opinion for PCT/US2007/013223 mailed Nov. 26, 2007.
International Search Report and Written Opinion for PCT/US2009/039507 mailed Jul. 14, 2009.
International Search Report and Written Opinion for PCT/US2009/039578 mailed Jul. 31, 2009.
International Search Report and Written Opinion for PCT/US2009/056670 mailed Mar. 2, 2010 claiming benefit of U.S. Appl. No. 12/211,407, filed Sep. 16, 2008 (which is a CIP of U.S. Appl. No. 12/039,849, filed Feb. 29, 2008, which is a CIP of U.S. Appl. No. 11/971,390, filed Jan. 9, 2008, which is a CIP of U.S. Appl. No. 11/756,957, filed May 31, 2007).
International Search Report and Written Opinion mailed Apr. 22, 2010 for PCT/US2010/024579 claiming benefit of U.S. Appl. No. 12/389,930, filed Feb. 20, 2009.
Invitation to Pay Additional Fees with Partial International Search mailed Nov. 26, 2009 for PCT/US2009/056670.
Kaus, Michael R., Ph.D., "Automated Segmentation of MR Images of Brain Tumors," Radiology, vol. 218, No. 2, (2001) pp. 586-591.
Klein, M., "Robot assisted insertion of craniofacial implants—clinical experience," CARS 2001, pp. 133-138 (2001) Elsevier Science B.V.
Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.
Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.
Nicholls, Paul, M.D., "Trauma Grand Rounds PMI (Patient-Matched Implants)" brochure, Biomet Orthopedics, Inc., (Feb. 29, 2000) 1 page.
Overhoff, H.M., et al., "Total Knee Arthroplasty: Coordinate System Definition and Planning based on 3-D Ultrasound Image Volumes," CARS 2001, pp. 283-288, (2001) Elsevier Science B.V.
Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.
Portheine, F., et al., Entwicklung eines klinischen Demonstrators für die computerunterstützte Orthopädische Chirurgie mit CT-Bildbasierten Individualschablonen, Bildverarbeitung für die Medizin (1998) 5 pages.
Portheine, K., "Development of a clinical demonstrator for computer assisted orthopedic surgery with CT-image based individual templates," Computer Assisted Radiology and Surgery, pp. 944-949, (1997) Elsevier Science B.V.
Radermacher, "Computer Assisted Orthopaedic Surgery with Image Based Individual Templates," Clinical Orthopaedics and Related Research No. 354, pp. 28-38 (1998) Lippincott Williams & Wilkins.
Radermacher, K., et al., "Computer Integrated Orthopaedic Surgery: Connection of Planning and Execution in Surgical Intervention," Computer-integrated surgery: technology and clinical applications, (1996) pp. 451-463.
Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.
Radermacher, K., et al., "Image Guided Orthopedic Surgery Using Individual Templates," Springer Berlin/Heidelberg, CVRMed-MRCAS'97, vol. 1205/1997 pp. 606-615).
Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.
Schuller-Götzburg, P., et al., 3D-Implantatplanung und Stereolithographie-Implantatbohrschablonen, Stomatologie 101.3, pp. 55-59 (2004).
Sharp, S. Michael, Ph.D, Patient-Specific, Resurfacing Bi-Compartmental Arthuroplasty, Futuretech, Orthopaedic Product News (Mar./Apr. 2008) pp. 12-15.
Sisto, Domenick, J., et al., "Custom Patellofemoral Arthroplasty of the Knee Surgical Technique," Journal of Bone and Joint Surgery, vol. 89-A, pp. 214-225 (2007).
Slammin, John et al, "Do You Have This Implant in My Size?", MDT Medical Design Technology, 3 pages, http://www.mdtmag.com/scripts/ShowPR.asp?PUBCODE=046&ACCT=0007796& ISSUE . . . accessed Jul. 31, 2008.
Steinwachs, Matthias Reinhard, "Cartilage Repair—Autologous Chondrocyte Transplantation and Autologous Matrix-induced Chondrogenesis," European Musculoskeletal Review (2006) pp. 65-68.
"Amazing Precision. Beautiful Results. The next evolution of MAKOplasty® is here," brochure. (Feb. 2009) MAKO Surgical Corp. 6 pages.
"Ascent Total Knee System," brochure. Biomet, Inc. (1999) 16 sheets.
"Customized Patient Instruments, Patient specific instruments for patient specific needs," brochure. (2008) DePuy Orthopaedics, Inc. 14 sheets.
"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.
"Discovery® Elbow System Surgical Technique," brochure. Biomet Orthopedics, Inc. (2008) pp. 1-25.
"Discovery® Elbow System," brochure. Biomet Orthopedics, Inc. (2007) 3 sheets.
"Hipsextant Instructions of Use." (2011) Surgical Planning Associates, Inc. 19 pages.
"Knee tensor combined with laser femoral head locator," Research Disclosure. Jul. 2006. No. 507; p. 903.
"Method for constructing an allograft sleeve." Research Disclosure (Dec. 2003) No. 476, p. 1294.
"OSS™ Orthopaedic Salvage System, Femoral/Tibial Augmentation," brochure. Biomet Orthopedics, Inc., (2003) pp. 1-8 (12 sheets).
"Regenerex® Tibial Cone Augment, Surgical Technique Addendum to the Vanguard® SSK Revision System," brochure. Biomet® Orthopedics. (2009) pp. 1-8 (12 sheets).
"Signature™ Personalized Patient Care, Surgical Technique Addendum to the Vanguard Knee System" brochure. Biomet® Orthopedics, Inc. (2009) pp. 1-8.
"TruMatch™ Personalized knee replacement solutions," tri-fold brochure. (2009) SIGMA® DePuy Orthopaedics, Inc. 2 pages.
"Vanguard® PFR Partial Knee Patellofemoral Replacement System," Surgical Technique brochure. Biomet Orthopaedics, (2010) pp. 1-25.
"Zimmer® UniSpacer® Knee System," brochure. (2005) Zimmer, Inc. 4 sheets.

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Kelly, Todd C., M.D., "Role of Navigation in Total Hip Arthroplasty." The Journal of Bone & Joint Surgery(2009) pp. 153-158. vol. 91-A, Supplement 1.

Murphy, S.B., et al. "The Hip Sextant: Navigation of Acetabular Component Orientation Using a Mechanical Instrument," brochure. (2009) 1 page.

Radermacher, Klaus, et al. "Computer Assisted Orthopaedic Individual Templates." Clinical Orthopaedics and Related Research. (Sep. 1998) No. 354; pp. 28-38.

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report mailed Nov. 30, 2010 for PCT/EP2010/061630 filed Aug. 10, 2010 claiming benefit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

International Preliminary Report on Patentability for PCT/US2010/050701 mailed Apr. 12, 2012 claiming benefit of U.S. Appl. No. 12/571,969, filed Oct. 1, 2009.

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D- computertomographischen Subtraktionsverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

* cited by examiner

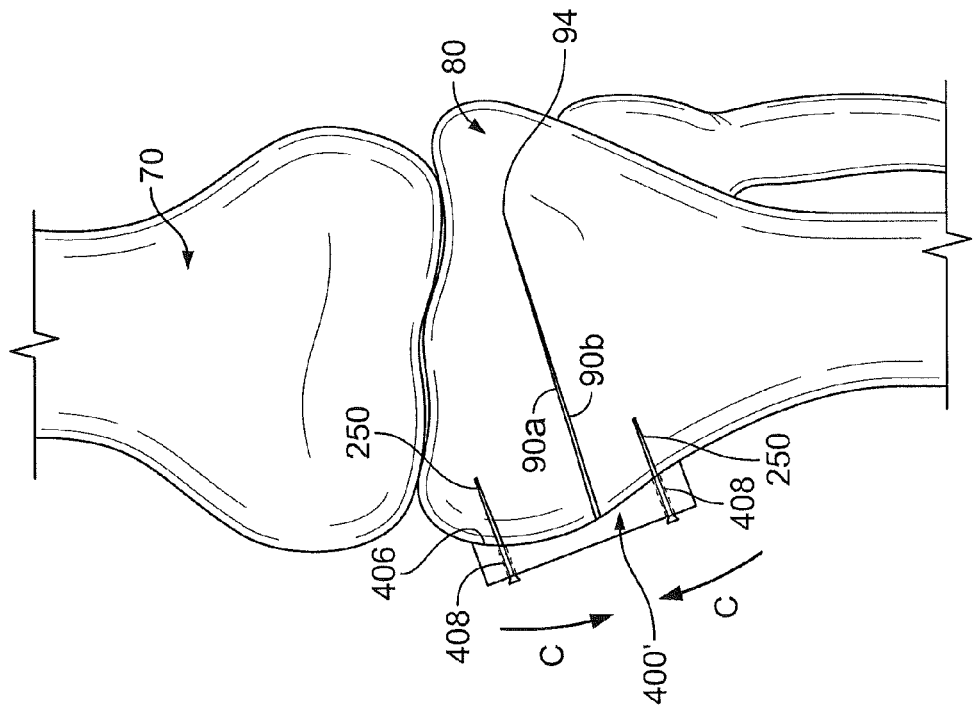
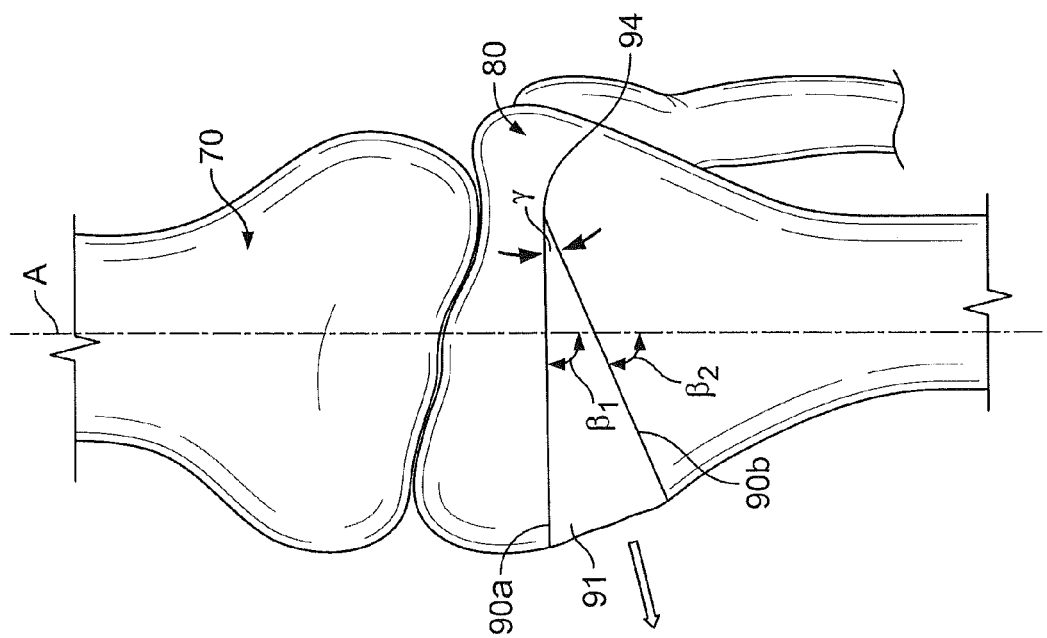
FIG. 4
FIG. 5

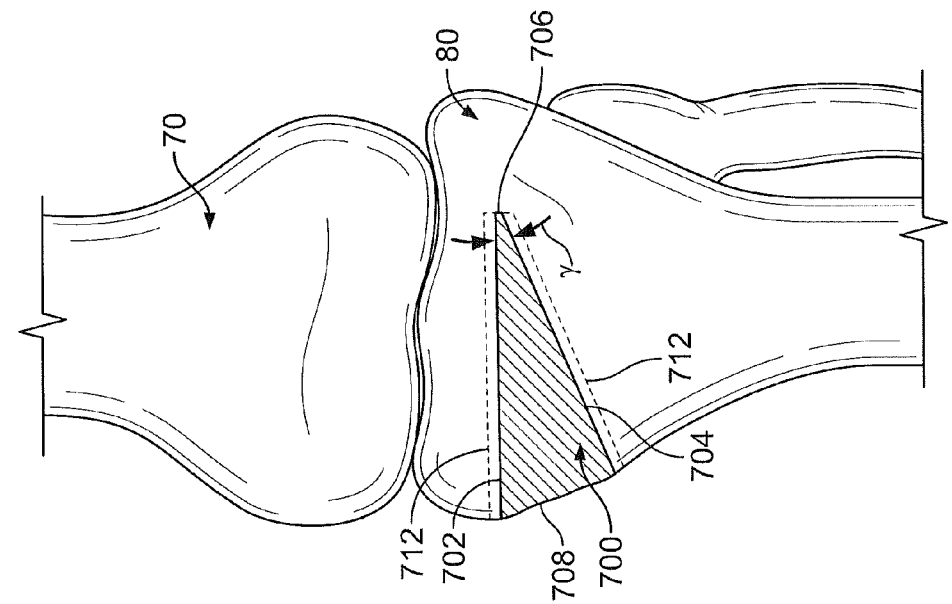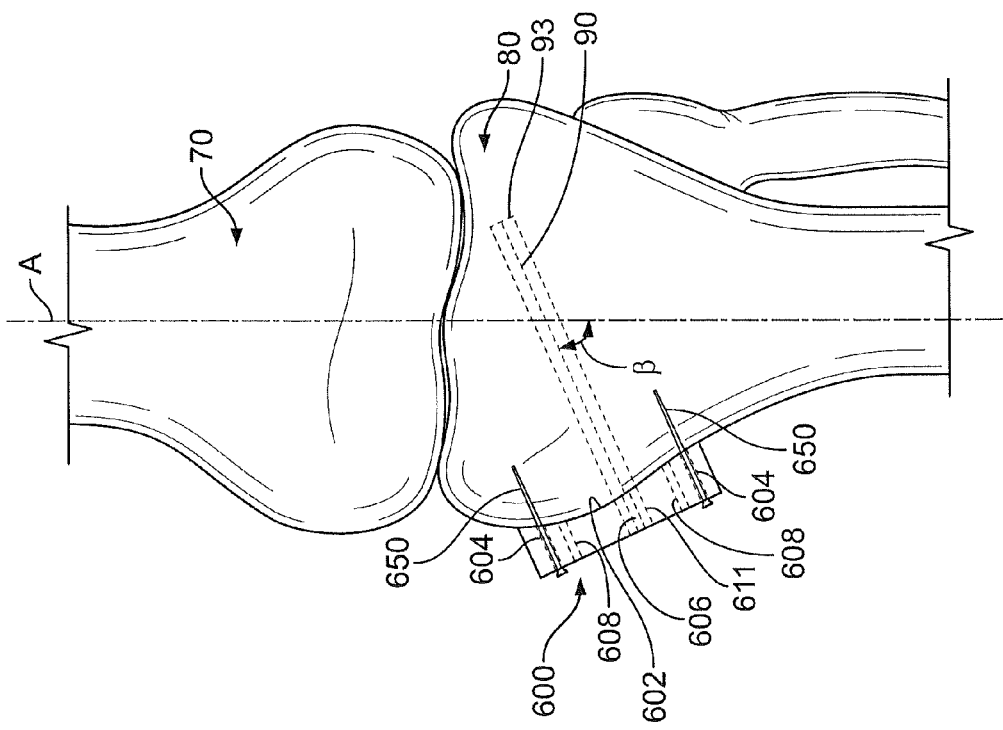

PATIENT SPECIFIC HIGH TIBIA OSTEOTOMY

CROSS-REFERENCE TO RELATED APPLICATIONS

This application is a continuation-in-part of U.S. application Ser. No. 12/571,969, filed Oct. 1, 2009, which is a continuation-in-part of U.S. application Ser. No. 12/389,901, filed Feb. 20, 2009, which is a continuation-in-part of U.S. application Ser. No. 12/211,407, filed Sep. 16, 2008, which is a continuation-in-part of U.S. application Ser. No. 12/039, 849, filed Feb. 29, 2008, which: (1) claims the benefit of U.S. Provisional Application No. 60/953,620, filed on Aug. 2, 2007, U.S. Provisional Application No. 60/947,813, filed on Jul. 3, 2007, U.S. Provisional Application No. 60/911,297, filed on Apr. 12, 2007, and U.S. Provisional Application No. 60/892,349, filed on Mar. 1, 2007; (2) is a continuation-in-part U.S. application Ser. No. 11/756,057, filed on May 31, 2007, which claims the benefit of U.S. Provisional Application No. 60/812,694, filed on Jun. 9, 2006; (3) is a continuation-in-part of U.S. application Ser. No. 11/971,390, filed on Jan. 9, 2008, which is a continuation-in-part of U.S. application Ser. No. 11/363,548, filed on Feb. 27, 2006; and (4) is a continuation-in-part of U.S. application Ser. No. 12/025,414, filed on Feb. 4, 2008, which claims the benefit of U.S. Provisional Application No. 60/953,637, filed on Aug. 2, 2007.

This application is also a continuation-in-part of U.S. application Ser. No. 12/103,834, filed Apr. 16, 2008, which claims the benefit of U.S. Provisional Application No. 60/912,178, filed Apr. 17, 2007.

This application is also a continuation-in-part of U.S. application Ser. No. 12/483,807, filed on Jun. 12, 2009, which is a continuation-in-part of U.S. application Ser. No. 12/371, 096, filed on Feb. 13, 2009, which is a continuation-in-part of U.S. application Ser. No. 12/103,824, filed on Apr. 16, 2008, which claims the benefit of U.S. Provisional Application No. 60/912,178, filed on Apr. 17, 2007.

The disclosures of the above applications are incorporated herein by reference.

INTRODUCTION

Various knee osteotomies are performed to adjust or change the orientation of the tibia to correct various abnormalities caused by birth defects, trauma, or disease. High tibial osteotomies include open-wedge and closed-wedge osteotomies. Various cutting instruments and tools are used to perform such high tibial osteotomies.

The present teachings provide patient patient-specific surgical kits and methods for open-wedge or closed-wedge tibial osteotomies.

SUMMARY

The present teachings provide a surgical kit that includes a patient-specific alignment guide having a three-dimensional engagement surface custom-made by computer imaging to conform to a corresponding portion of a patient's tibial bone. The patient-specific alignment guide defines an elongated planar slot for guiding a blade. The planar slot is oriented at a selected angle and at a selected position relative to an anatomic axis of the patient when the engagement surface engages the corresponding portion of the tibial bone. The selected angle and selected position are determined during a pre-operative planning stage.

The present teaching also provide a surgical kit that includes a patient-specific implantable wedge for an open-wedge osteotomy, a patient-specific fixation plate and a patient-specific alignment guide. The implantable wedge includes first and second planar surfaces defining a patient-specific wedge angle, and a patient-specific outer surface opposite to the straight edge. The patient-specific fixation plate has a three-dimensional patient specific engagement surface for engaging the tibia and a surface engageable with the implantable wedge. The patient-specific alignment guide includes an engagement surface custom-made by computer imaging to conform to a corresponding portion of a patient's tibial bone. The patient-specific alignment guide defines an elongated planar slot for guiding a blade. The planar slot is oriented at a selected angle and at a selected position relative to an anatomic axis of the patient when the engagement surface engages the corresponding portion of the tibial bone. The selected angle and selected position are determined during a pre-operative planning stage.

The present teaching provide a surgical method including attaching a patient-specific alignment guide to a corresponding surface of a tibia of a patient for whom the alignment guide is customized during a pre-operative planning stage and making a partial bone cut in the tibia through a planar slot of the alignment guide. The planar slot is oriented at a patient-specific angle relative to an anatomic axis of the patient and the angle is customized during the pre-operative planning stage. The method includes opening the bone cut to form an opening wedge, and inserting a patient-specific implantable wedge into the opening wedge.

The present teaching provide a surgical method including attaching a patient-specific alignment guide to a corresponding surface of a tibia of a patient for whom the alignment guide is customized during pre-operative planning and making a first partial planar cut in the tibia through a first planar slot of the alignment guide. The first planar slot is oriented at a first patient-specific angle relative to an anatomic axis of the patient and the first angle customized during a pre-operative planning stage. A second partial planar cut is made in the tibia through a second planar slot of the alignment guide. The second planar slot is oriented at a second patient-specific angle relative to an anatomic axis of the patient and the second angle is customized during the pre-operative planning stage. The first and second planar cuts meet at an angle to define a bone wedge having a third patient-specific angle. The method includes removing the bone wedge to form a wedge opening and closing the wedge opening.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 4 is a schematic illustration of removing a bone wedge for closed-wedge high tibial osteotomy in relation to the present teachings;

FIG. 5 is a schematic illustration of closing the wedge opening of FIG. 4 and attaching one fixation plate;

FIG. 11 is an environmental view of the patient-specific guide of FIG. 10 according to present teachings;

FIG. 13 is an environmental view of the patient-specific wedge implant of FIG. 11 according to present teachings.

DESCRIPTION OF VARIOUS ASPECTS

Figure 2:
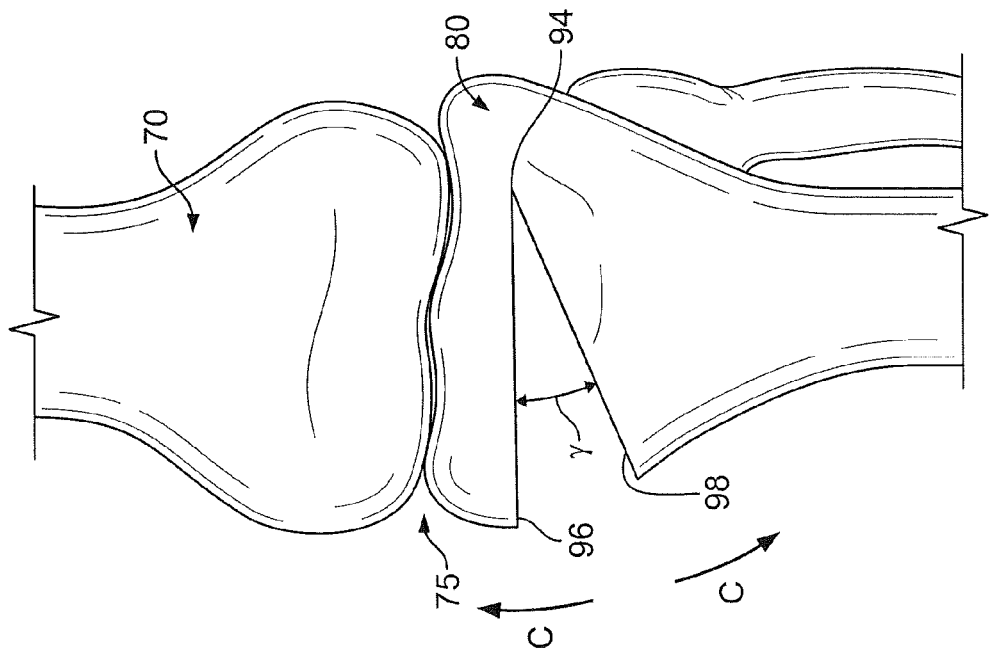
FIG. 2 is a schematic illustration of opening the cut of FIG. 1 to form an wedge opening.

The following description is merely exemplary in nature and is in no way intended to limit the present teachings, applications, or uses. For example, although the present teachings are illustrated for patient-specific instruments and implants for high tibial osteotomy, the present teachings can be used for other types of osteotomy procedures.

The present teachings generally provide patient-specific surgical kits that include alignment guides and associated implant components for use in osteotomy, such as high tibial osteotomy, for example. The patient-specific alignment guides can be used either with conventional or patient-specific implant components prepared with computer-assisted image methods. Computer modeling for obtaining three dimensional images of the patient's anatomy using MRI or CT scans of the patient's anatomy, the patient specific prosthesis components, and the patient-specific guides and templates can be provided by various CAD programs and/or software available, for example, by Materialise USA, Ann Arbor, Mich.

The patient-specific alignment guides and associate patient-specific implants disclosed herein can be generally formed using computer modeling based on the patient's 3-D anatomic image generated from image scans. The patient-specific alignment guides can have a three-dimensional engagement surface that is made to conformingly contact and match a three-dimensional image of the patient's bone surface (selectively with or without soft tissue), by the computer methods discussed above. The patient-specific alignment guides can include custom-made guiding formations, such as, for example, guiding bores or cannulated guiding posts or cannulated guiding extensions or receptacles that can be used for supporting or guiding other instruments, such as drill guides, reamers, cutters, cutting guides and cutting blocks or for inserting pins or other fasteners according to a surgeon-approved pre-operative plan.

In various embodiments, the patient-specific alignment guide can include one or more patient-specific cutting guides for receiving and guiding a cutting blade at corresponding patient-specific cutting plane orientations relative to a selected anatomic axis for the specific patient. The patient-specific alignment guides can also include guiding formations for guiding the implantation of patient-specific or off-the-shelf implants associated with the osteotomy procedure, such as implantable wedges and implantable fixation plates. The geometry, shape and orientation of the various features of the patient-specific alignment guide, as well as various patient-specific implants and other patient-specific tools can be determined during the pre-operative planning stage of the procedure in connection with the computer-assisted modeling of the patient's anatomy. During the pre-operative planning stage, patient-specific alignment guides, implants and other tools, can be selected and manufactured for a specific-patient with input from a surgeon or other professional associated with the surgical procedure, as described in the commonly assigned and co-pending patent applications listed in the cross reference section and incorporated herein by reference.

In the following discussion, the terms "patient-specific", "custom-made" or "customized" are defined to apply to components, including tools, implants, portions or combinations thereof, which include certain geometric features, including surfaces, curves, or other lines, and which are made to closely conform as mirror-images or negatives of corresponding geometric features of a patient's anatomy during a pre-operative planning stage based on 3-D computer images of the corresponding anatomy reconstructed from image scans of the patient by computer imaging methods. Further, patient specific guiding features, such as, guiding apertures and guiding slots, or other holes or openings that are included in alignment guides or in implants are defined as features that are made to have positions, orientations, dimensions, shapes and and/or define cutting planes specific to the particular patient's anatomy based on the computer-assisted pre-operative plan associated with the patient.

Figure 3B:
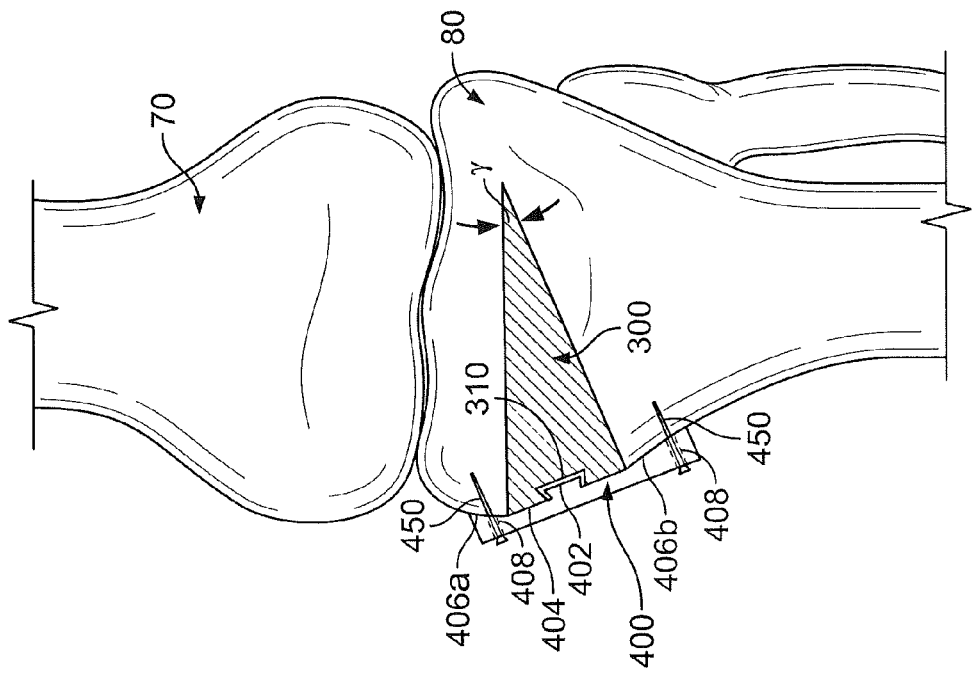
FIG. 3B is an environmental sectional view of a patient-specific plate and a patient-specific wedge of open-wedge high tibial osteotomy according to the present teachings.
Figure 3A:
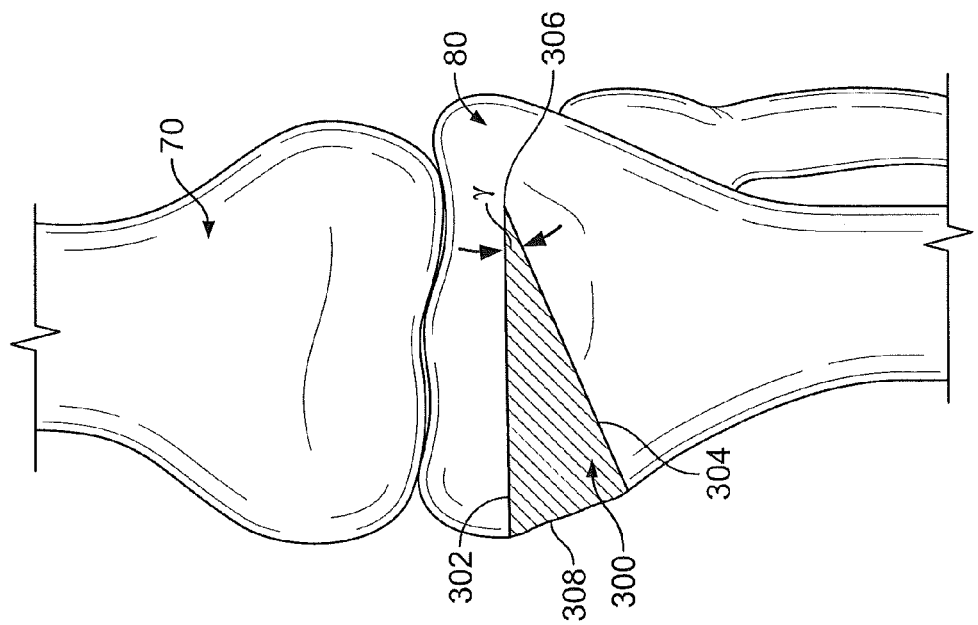
FIG. 3A is an environmental sectional view of a patient-specific wedge for the wedge opening of FIG. 2 according to the present teachings.
Figure 6:
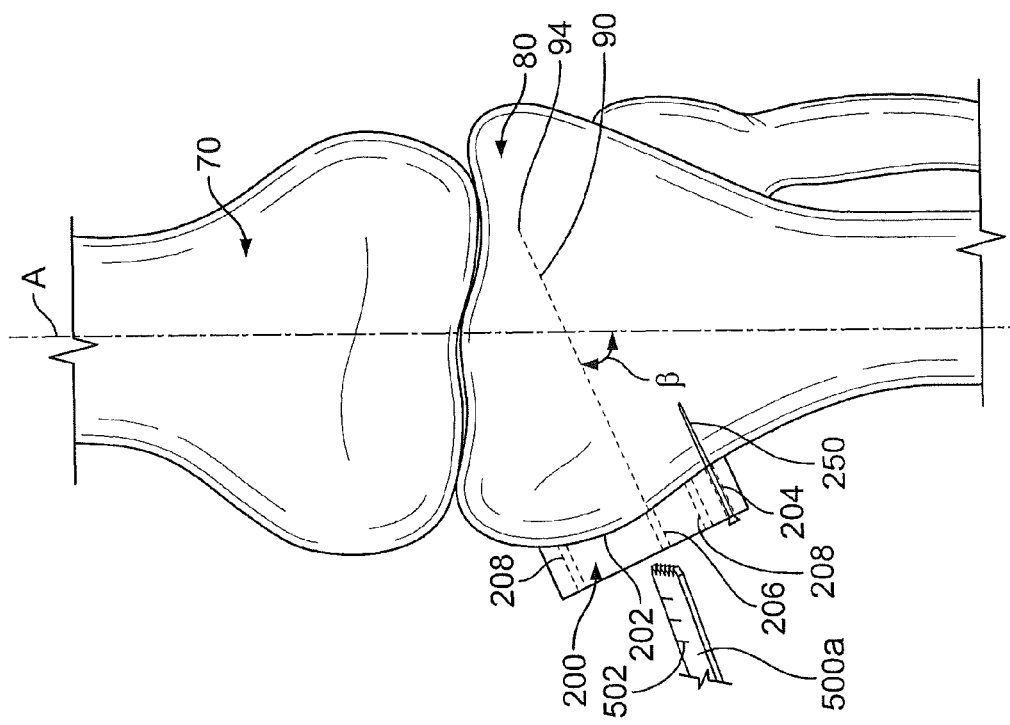
FIG. 6 is an environmental view of a patient-specific guide for an open-wedge high tibial osteotomy in relation to the present teachings.

A patient-specific osteotomy kit for an open-wedge osteotomy can include, according to the present teachings, a patient-specific alignment guide 200, as shown in FIG. 6, for example, a patient-specific implantable wedge (or wedge implant) 300, as shown in FIGS. 3A-3B, for example, and a patient-specific implantable fixation plate 400, as shown in FIG. 5, for example. The implantable wedge 300 and a patient-specific implantable fixation plate 400 can be modularly connected, or alternatively formed monolithically as a single integral structure. An off-the-shelf, i.e. non patient-specific implantable wedge or an off-the-shelf, i.e. non patient-specific implantable fixation plate can also be used optionally with the patient-specific alignment guide 200. For closed-wedge osteotomies, the implantable wedge 300 is omitted. It will be appreciated that the patient-specific alignment guides for open-wedge and closed-wedge osteotomies can include different features, as discussed below.

The patient-specific osteotomy kit can also include custom-made saw blades 500a, 500b having a predetermined cutting length corresponding to a patient-specific cutting depth. The cutting depth can be determined at the pre-operative planning stage. In various embodiments, the predetermined cutting length can be an actual dimension of the cutting edge of the blade 500*b* (see FIG. 9). In various other embodiments, the cutting depth can be adjustable and the blade 500*a* can include markings 502 indicating a patient-specific cutting depth. The cutting depth can also be constrained by a depth stop engaging the patient-specific alignment guide 200 at a patient-specific depth and preventing insertion of the cutting blade beyond the pre-determined length. A separate, commercially available depth gauge can also be used to mark and restrict cutting to a pre-determined patient-specific cutting depth.

Figure 1:
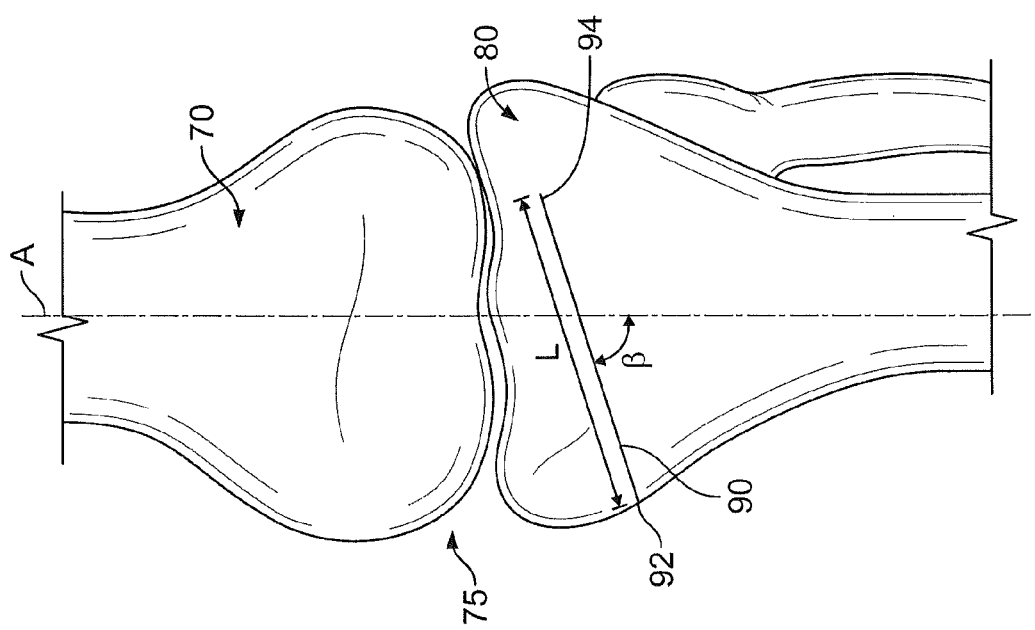
FIG. 1 is a schematic illustration of a cut for open-wedge high tibial osteotomy in relation to the present teachings.

Referring to FIGS. 1 and 2, an exemplary open-wedge high tibial osteotomy is illustrated in association with a knee joint 75 between a femur 70 and a tibia 80. A planar cut 90 at a selected angle β relative to a first reference axis A of the knee joint 75 can be made using the patient-specific kit of the present teachings. The first reference axis A can be a selected anatomic axis, such as, for example a mechanical axis of the joint or leg, a mechanical axis of the femoral bone, or a mechanical axis of the tibial bone, when different from the mechanical axis of the leg. Other anatomic axes, such as axes having significantly different orientations than the orientation of axis A illustrated in FIG. 1, can be used as reference axes, including, for example, an epicondylar axis, which can be substantially transverse to the axis A of FIG. 1. The angle β of the planar cut 90 relative to the reference axis A can be determined during the pre-operative planning stage of the osteotomy and in relation to the corresponding alignment guide 200.

Figure 1A:
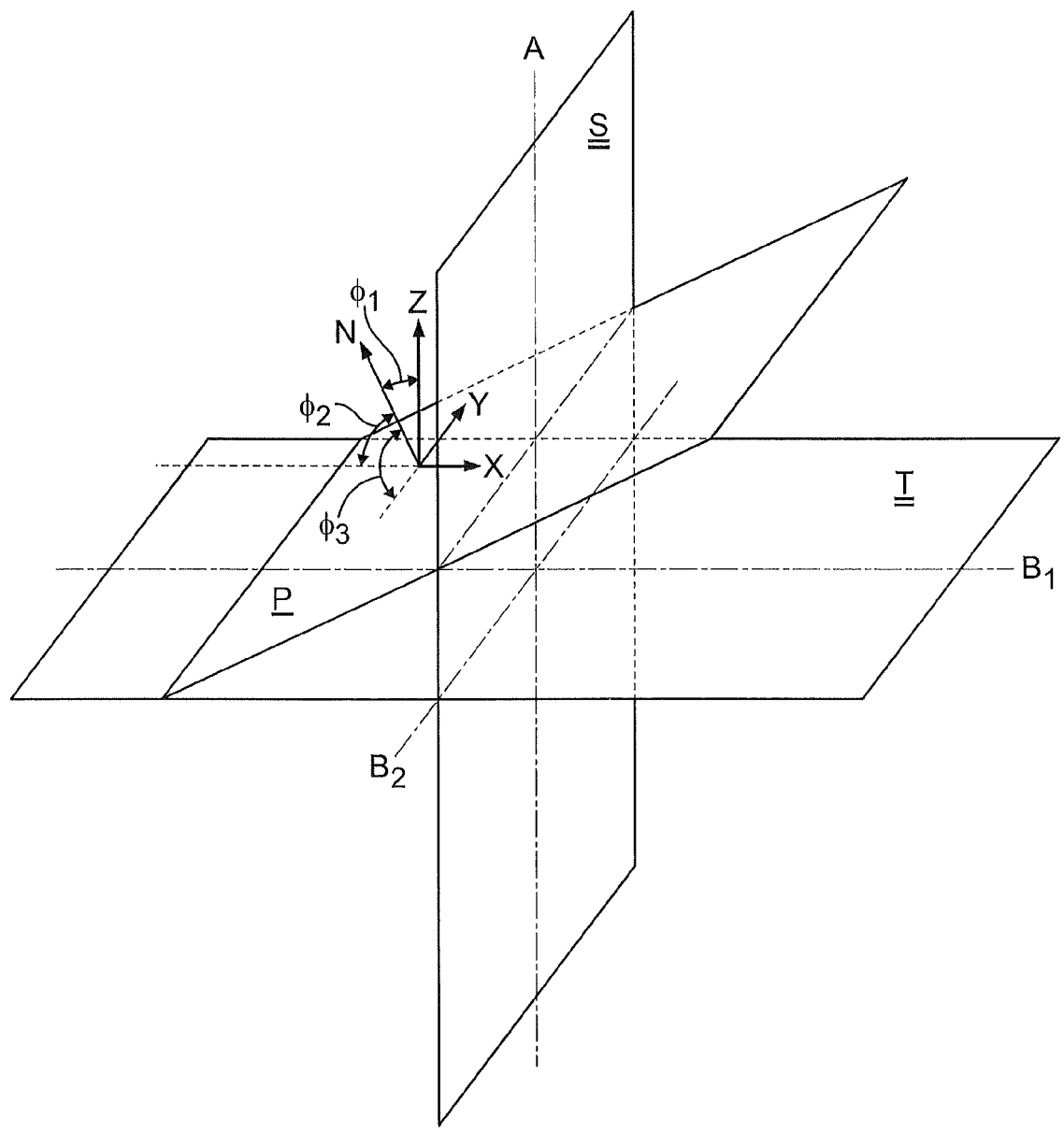
FIG. 1A is a schematic illustration of the geometry of an exemplary cut plane in relation to anatomic sagittal and transverse planes according to the present teachings.

The planar cut 90 can also be oriented at a patient-specific angle relative to second and third reference axes $B_1$ and $B_2$. A representative geometry illustrating the orientation of an exemplary cut plane P in relation to a sagittal plane S and a transverse plane T of the patient's anatomy is shown in FIG. 1A. In FIG. 1A, a first angle $\phi_1$ is defined between an axis N perpendicular to the cut plane P and an axis z parallel to the first reference axis A, which extend superiorly-inferiorly on the sagittal plane. The first angle $\phi_1$ and angle β have a sum of 90 degrees. A second angle $\phi_2$ is defined between the axis N and an axis x parallel to the second reference axis $B_1$, which extends medially-laterally on the transverse plane T. A third angle $\phi_3$ is defined between the axis N and an axis y parallel to the third reference axis $B_2$, which extends anteriorly-posteriorly on the transverse plane T. Medial-lateral, anterior-posterior and superior-inferior orientations of the cut plane P can be specified by selecting patient specific values for these angles, keeping in mind that only two of the three angles can be specified independently, while the third can be calculated from the relation that the sum of the squares of the cosines of the angles is equal to 1. In the following discussion, although patient-specific orientations of planar cuts and corresponding planar slots relative to the axis A will be described in detail, it will be understood that the planar cuts and planar slots can be additionally or alternatively be oriented at patient-specific angles about the axes $B_1$ and $B_2$.

Referring to FIGS. 1-3, the planar cut 90 is a partial cut, i.e., not a through cut, and can extend from a first boundary 92 at the intersection of the planar cut 90 with the outer surface of the tibia 80 to a second boundary 94 at the selected patient-specific cutting depth illustrated as distance L in FIG. 1. The first boundary 92 can be generally a curved line reflecting the curvature of the outer surface of the tibia 80. The second boundary 94 can be substantially a straight line as formed by the saw blade. The second boundary 94 can function as a hinge line (also referenced with numeral 94) for opening a wedge angle γ between first and second opposing faces 96, 98 of the cut 90, as illustrated by arrows C in FIG. 2. The wedge angle γ is patient-specific and can be selected during the pre-operative planning stage. The location of the first and second boundaries 92, 94, the angle β of the planar cut 90 relative to the reference axis A and the wedge angle γ can be determined during the pre-operative planning stage for correcting a condition of the particular patient, including conditions resulting from idiopathic bone misalignment, joint or bone disease, trauma, cancer or other therapeutic or corrective surgery. Similarly, the planar cut 90 can be oriented at a corresponding patient-specific angle $\phi_2$ relative to the medial-lateral axis $B_1$, as illustrated in FIG. 1A.

Referring to FIGS. 1-3A, a patient-specific implantable wedge 300 having a corresponding wedge angle γ defined between first and second planar surfaces 302, 304 can be inserted and/or pushed between the first and second faces 96, 98 of the cut 90, while the cut 90 is partially open, i.e., while the first and second faces 96, 98 form an angle smaller than the angle γ, for guiding and facilitating the correct wedge opening to form the pre-selected angle γ. It will be appreciated, however, the cut 90 can be opened to an angle γ, using any other tool, such as trial wedge having the same angle γ.

With continued reference to FIGS. 1-3A, the first and second first and second planar surfaces 302, 304 of the implantable wedge 300 can meet at a straight edge or truncated plane surface 306. Upon insertion of the implantable wedge 300, the cut 90 is opened and secured to the selected angle γ by the implantable wedge 300. The first and second planar surfaces 302, 304 of the implantable wedge 300 can abut against the first and second surfaces 96, 98 of the planar cut 90, and the edge 306 of the implantable wedge 300 can abut the second boundary 94 of the planar cut 90. The implantable wedge 300 can have a patient-specific boundary surface 308 opposite to the edge/surface 306. The boundary surface 308 is designed during the pre-operative planning stage as a continuous and smooth surface that provides a continuous contour relative to the contour of the tibia 80 on either side of the cut 90. The implantable wedge 300 can also be secured directly in the bone with sutures, pins, anchors or other fasteners.

Alternatively, and referring to FIGS. 3A and 3B, a patient-specific implantable fixation plate 400 can be used in combination with the patient-specific implantable wedge 300. The patient-specific implantable wedge 300 and the patient-specific fixation plate 400 can be modularly connected, as illustrated in FIG. 3B, or can be provided as a single monolithic and integrally formed component. A modular connection can include a dovetail connection illustrated at reference numerals 402 and 310 corresponding to opposing connection formations of the fixation plate 400 and implantable wedge 300. Other connection formations can include a taper lock connection, various groove and tongue connections, or connections with threadable fasteners or other biocompatible fasteners. The modular connection can be formed at a common boundary 404 between the fixation plate 400 and the implantable wedge 300.

The fixation plate 400 can include patient-specific surfaces 406*a*, 406*b* on either side the implantable wedge 300 and can be anchored to the tibia 80 using bone pins or other bone fasteners 450 that pass through corresponding apertures 408 of the fixation plate 400. The location and orientation of the apertures can also be patient-specific and determined during the pre-operative planning stage for the particular patient.

In various embodiments, and referring to FIG. 6, a patient-specific alignment guide 200 for an open-wedge osteotomy is illustrated. The alignment guide 200 can include a three-dimensional patient-specific engagement surface 202 made to conform to a corresponding outer surface of the tibia 80 by a computer-assisted method utilizing a 3-D image of the patient's tibia 80 during the pre-operative planning stage, as discussed above. The alignment guide 200 can include one or more guiding receptacles, the precise location of which is determined on the basis of a pre-operative surgical plan for locating alignment pins or other fasteners or for assisting in locating cutting blades or other cutting instruments for resecting the bone and/or shaping the bone for receiving an implant, as described in commonly-owned, co-pending in U.S. patent application Ser. No. 11/756,057, filed on May 31, 2007, incorporated herein by reference. The alignment guide can be placed on and conform with the anterior/lateral surface of the tibia, for example.

Referring to FIG. 6, the alignment guide 200 can include a guiding receptacle in the form of a planar slot 206 oriented to define a patient-specific angle β relative to the anatomic axis A for guiding a blade 500a to form the planar cut 90. The blade 500a can include depth-control indicia 502 corresponding to the hinge line 94. The alignment guide 200 can also define one or more fixation apertures 204 for receiving bone fixation fasteners 250. Additional guiding receptacles, such as guiding apertures 208, can be provided for preparing fastener holes in the tibia 80 to receive the bone fixation fasteners 250 through the apertures 408 of the fixation plate 400. The location and orientation of the planar slot 206, the apertures 204 for the fasteners 250 and the guiding apertures 208 relative to alignment guide 200 can be determined during the pre-operative planning stage on a patient-specific (patient customized) basis. Similarly, the planar slot 206 can be oriented at a corresponding patient-specific angle $\phi_2$ relative to the medial-lateral axis $B_1$, as illustrated in FIG. 1A.

Figure 8:
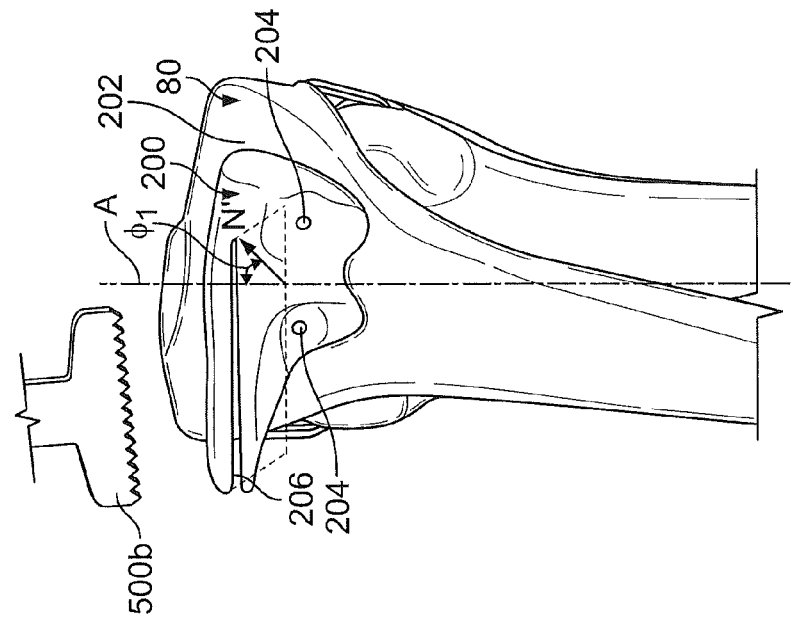
FIG. 8 is an environmental view of a patient-specific guide for an open-wedge high tibial osteotomy in relation to the present teachings.

Referring to FIG. 8, another alignment guide 200 for open-wedge osteotomy is illustrated. The alignment guide 200 can be placed on the anterior and/or lateral side of the proximal tibia 80, such that the three-dimensional patient-specific engagement surface 202 of the alignment guide 200 closely conforms to the corresponding portion of the tibia 80. The plane defined by the planar slot 206 is shown in phantom at a corresponding angle $\beta=90-\phi_1$ relative to the reference/anatomic axis A, as discussed above in connection with FIG. 6. A blade 500b can be used for the plane cut through the planar slot 206 having size that provides automatic control of the length of the cut.

Referring to FIGS. 4 and 5, an exemplary closed-wedge high tibial osteotomy is illustrated in association with a knee joint 75 between a femur 70 and a tibia 80. First and second partial planar cuts 90a, 90b at corresponding selected first and second angles $\beta_1$ and $\beta_2$ relative to a reference/anatomic axis A of the knee joint 75 can be made using a patient-specific kit of the present teachings. The first and second planar cuts 90a, 90b can intersect at a hinge line 94. The first and second angles $\beta_1$ and $\beta_2$ of the planar cuts 90a, 90b relative to the reference axis A can be determined during the pre-operative planning stage of the osteotomy and in relation to the corresponding alignment guide 200. Each of the first and second angles $\beta_1$ and $\beta_2$ is complementary of a corresponding angle $\phi_1$ shown in FIG. 1A ($90-\beta_1$ and $90-\beta_2$). Similarly, the first and second cuts 90a, 90b can be oriented at corresponding and different angles $\phi_2$ relative to the medial-lateral axis $B_1$, as illustrated in FIG. 1A. The first and second angles $\beta_1$ and $\beta_2$ of the planar cuts 90a, 90b define a bone wedge 91 of predetermined wedge angle $\gamma=\beta_1-\beta_2$. The bone wedge 91 can be removed and the corresponding wedge opening can be closed by bringing the surfaces of the first and second cuts 90a, 90b in contact by rotating about the hinge line 94. A first (or osteotomy-side) patient-specific fixation plate 400' can be attached to the tibia 80 to secure the first and second cuts 90a, 90b in contact after the bone wedge 91 is removed. The first and second cuts 90a, 90b can also be secured by pins, sutures or other fasteners to the bone. In the fixation plate 400' the same reference numerals are used to indicate features having the same functions as in the fixation plate 400. The fixation plate 400' can include a patient-specific engagement surface 406 and apertures 408 at patient-specific positions and orientations for guiding bone fixation fasteners 250 through the apertures 408 and into the tibia 80.

Figure 5A:
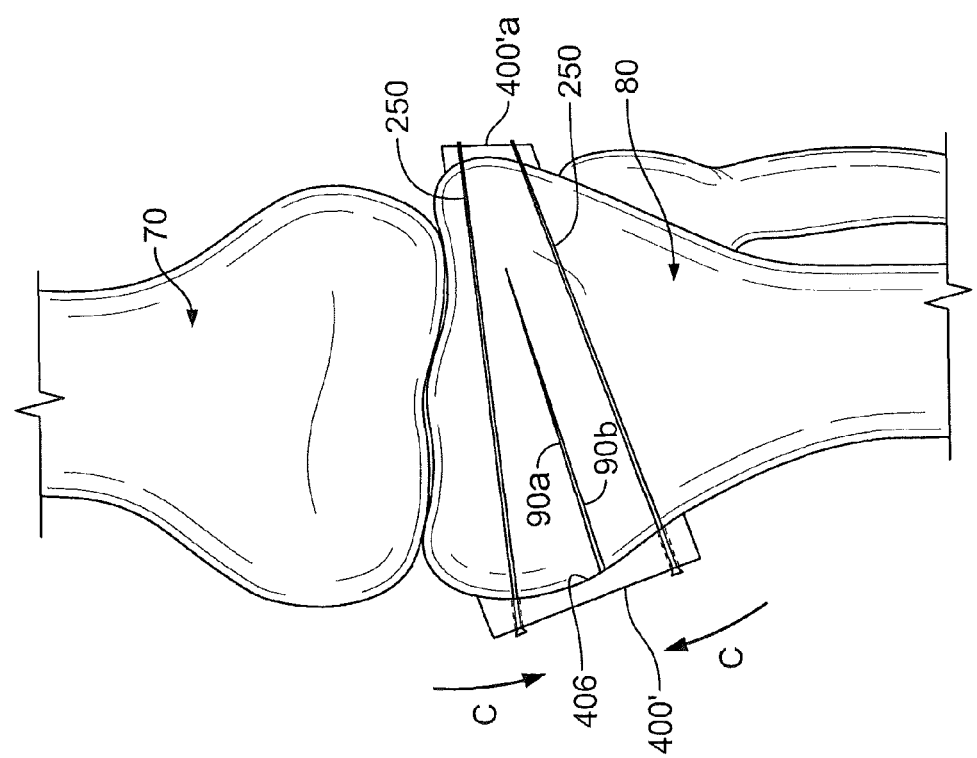
FIG. 5A is a schematic illustration of closing the wedge opening of FIG. 4 and attaching two fixation plates.

Referring to FIGS. 5 and 5A, a second (or hinge-side) fixation plate 400'a can be used opposite the first or osteotomy-side fixation plate 400' on the side of the osteotomy hinge. The second fixation plate 400'a can be a patient-specific fixation plate or an off-the shelf commercially available fixation plate. The second plate 400'a can be attached to the tibia with separate fasteners. Alternatively, the same fixation fasteners 250 can extend between both the first and second plates 400' and 400'a. In such case, the guiding apertures 208 of the alignment guide 200' can be used to drill guiding holes through the entire width of the tibia 80 for guiding the location of the first and second plates 400' and 400'a and the common fixation fasteners 250 through the tibia and through the first and second plates 400' and 400'.

Figure 7:
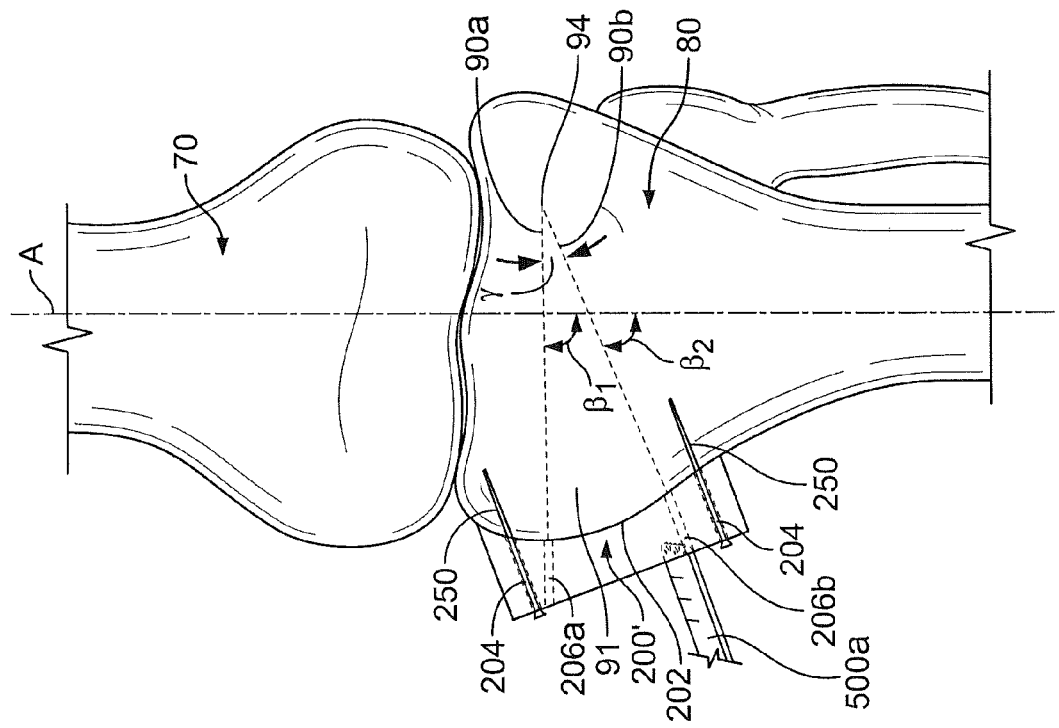
FIG. 7 is an environmental view of a patient-specific guide for closed-wedge high tibial osteotomy in relation to the present teachings.
Figure 10:
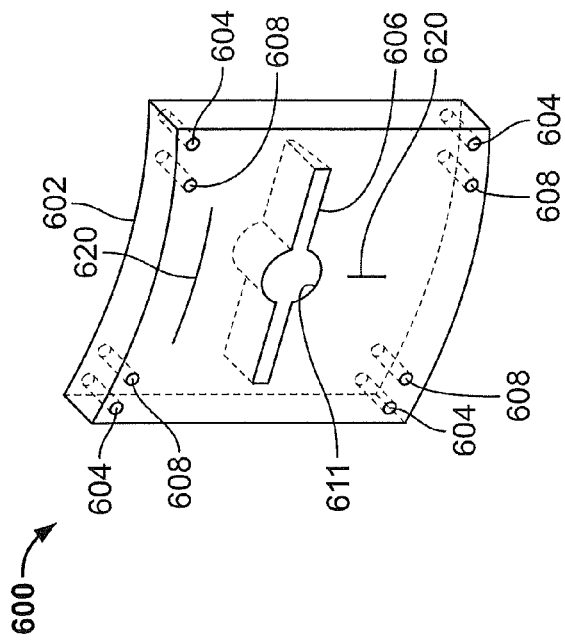
FIG. 10 is an isometric view of a patient-specific guide according to present teachings.

Referring to FIG. 7, a patient-specific alignment guide 200' for a closed-wedge osteotomy is illustrated. In alignment guide 200' the same reference numerals are used to indicate features having the same functions as in alignment guide 200. The alignment guide 200' can include a three-dimensional patient-specific engagement surface 202 made to conform to a corresponding outer surface of the tibia 80 by a computer-assisted method utilizing a 3-D image of the patient's tibia 80 during the pre-operative planning stage, as discussed above. The alignment guide 200' can define first and second guiding receptacles in the form of first and second planar slots 206a, 206b oriented at selected first and second angles $\beta_1$ and $\beta_2$ relative to a reference/anatomic axis A for guiding a blade to form the planar cuts 90a, 90b of the removable bone wedge 91. The alignment guide 200' can also define one or more apertures 204 receiving bone fixation fasteners 250. Additional guiding receptacles, such as guiding apertures 208 can be provided for drilling or otherwise preparing fastener holes in the tibia 80 corresponding to the apertures 408 of the fixation plate 400 for securing the fixation plate 400 to the tibia 80. The location and orientation of the first and second planar slots 206a, 206b, the apertures 204 and the guiding apertures 208 relative to alignment guide 200' can be determined during the pre-operative planning stage on a patient-specific base. The alignment guide 200' can be used with a blade 500a having depth indicia 502.

Figure 9:
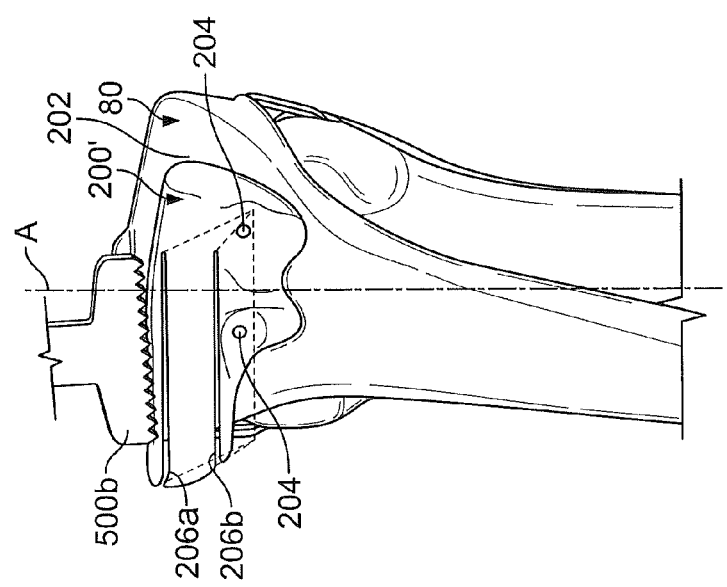
FIG. 9 is an environmental view of a patient-specific guide for closed-wedge high tibial osteotomy in relation to the present teachings.

Referring to FIG. 9, another alignment guide 200' for closed-wedge osteotomy is illustrated. The alignment guide 200' can be placed on the anterior and/or lateral side of the proximal tibia 80, such that the patient-specific engagement surface 202 of the alignment guide 200' closely conforms to the corresponding portion of the tibia 80. The planes defined by the first and second planar slots 206a, 206b are shown in phantom at corresponding first and second angles $\beta_1$ and $\beta_2$ (not shown) relative to the reference/anatomic axis A, as discussed above in connection with FIG. 7 and FIG. 1A. Additionally and optionally, each of the first and second angles $\beta_1$ and $\beta_2$ is complementary of a corresponding angle $\phi_1$ shown in FIG. 1A ($90-\beta_1$ and $90-\beta_2$). Similarly, the planes defined by the first and second planar slots 206a, 206b can be oriented at corresponding and different angles $\phi_2$ relative to the medial-lateral axis $B_1$, as illustrated in FIG. 1A.

Referring to FIGS. 10-13, another embodiment of a patient-specific alignment guide is illustrated at 600. As in the embodiments discussed above, the patient-specific alignment guide includes a three-dimensional patient-specific engagement surface 602, fixation apertures 604 for bone fixation fasteners 650 and guiding apertures 608 for drilling holes in the bone. In this embodiment, the alignment guide 600 includes a central cylindrical through-hole 611 passing through the center of a planar slot 606. The central hole 611, which has a diameter greater than the opening of the slot 606, can facilitate cutting with a blade along the slot 606 through either side of the central hole 611. Referring to FIG. 11, the central hole 611 of the alignment guide 600 can be used to drill a hole 93 in the bone 80 before the planar osteotomy cut 90 is performed at a selected patient-specific angle β, as shown in FIG. 11. The patient-specific guide 600 can include radiolucent markers 620, which are visible in radiographic images and can provide directional guidance during the surgical procedure. Similar markers in the form of lines or points/spots can also be provided on the patient-specific alignment guides 200, 200' discussed above.

Figure 12:
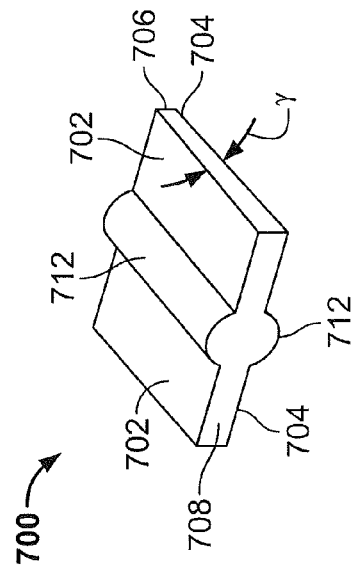
FIG. 12 is an isometric view of an exemplary implantable wedge according to present teachings.

Referring to FIGS. 12 and 13, a patient-specific implantable wedge 700 can be inserted through the osteotomy cut to keep the osteotomy open. Similarly to the embodiments described above, the implantable wedge 700 can include a three-dimensional patient-specific surface 708 (best shown in FIG. 13), an elongated curved central portion 712 conforming to shape of the drilled hole 93 on the opposite surfaces of the planar cut 90. The elongated central portion 712 can be cylindrical or tapered (truncated cone or conical segment). A pair of planar portions 702, 704 extend radially from opposite sides of the central portion 712 from the patient specific surface 708 to an end surface 706 and define a wedge of angle γ. The central portion 712 can be aligned with the hole 93 and provide a guide for centering and inserting the implantable wedge 700 into the osteotomy cut 90. The central portion 712 can have greater thickness than and protrude away from and outside the planar portions 702, 704.

Figure 14A:
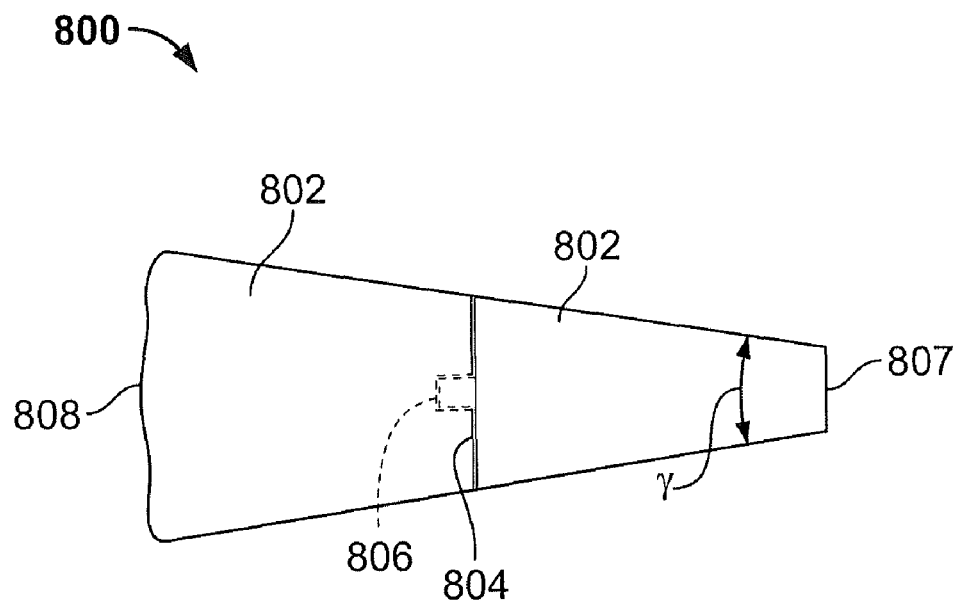
FIGS. 14A and 14B are plan views of exemplary implantable wedges according to present teachings.
Figure 14B:
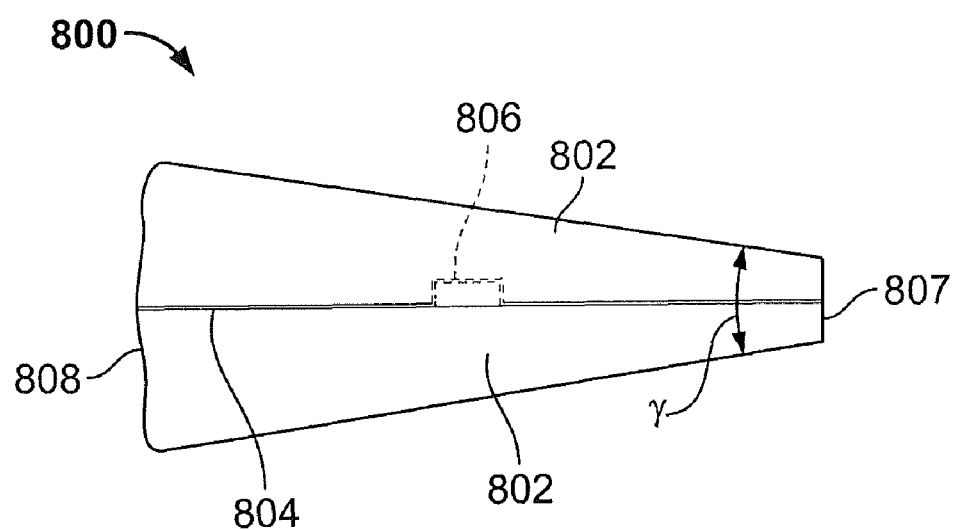

The various patient-specific implantable wedges 300, 700 for the open-wedge osteotomy can be made of various biocompatible materials including, for example, various metals or alloys, porous metal and porous metal alloys and bone-growth inducing materials, including Pro Osteon®, commercially available from Biomet, Inc., Warsaw, Ind., with or without a resorbable filler material. The implantable wedges 300, 700 can also be in the form of multiple-component wedges with or without interlocking connecting features. An exemplary illustration of a multiple-piece implantable wedge 800 is shown in FIGS. 14A and 14B. The implantable wedge 800 can extend from a first surface 808 to a second surface 807. The first surface 808 can be optionally patient-specific. The implantable wedge 800 can include a plurality of separate components 802. Two adjacent components 802 can be in contact at a common boundary 804. The adjacent components 802 can also be optionally interlocked with a connecting feature 806. The connecting feature 806 can be a single structural connector or a plurality of structural connectors, including tongue and groove, interdigitation, dovetail, threaded fasteners, etc.

The various fixation plates 400, 400', 400'a can be made of similar materials. For open-wedge osteotomies, the fixation plate 400 can be integral to the implantable wedge 300, modularly coupled to the implantable wedge 300 via a connecting joint or fasteners, or directly coupled to the bone outside the implantable wedge 300. The various alignment guides 200, 200', 600 can be made of any biocompatible material, including, polymer, ceramic, metal or combinations thereof.

As discussed above, a surgical kit for an open-wedge or a closed-wedge high tibial osteotomy can be provided on a patient-specific basis. The surgical kit can include a patient-specific alignment guide and, optionally, a patient-specific or an off-the-self fixation plate. For an open-wedge osteotomy, the surgical kit can include a patient-specific or an off-the-shelf implantable wedge. The patient-specific tools and implants are customized and prepared for the specific patient during a computer-assisted pre-operative planning stage in which the patient's anatomy is modeled in three dimensions from two-dimensional image scans. Patient-specific or customized blades can be included to provide adjustable depth control or automatic length. Other, non-customized blades can also be included.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the present teachings without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. A surgical kit comprising:
    a patient-specific alignment guide including a three-dimensional engagement surface custom-made by computer imaging to conform as a negative surface to a corresponding surface of a patient's tibial bone, the patient-specific alignment guide defining a first elongated planar slot for guiding a blade, the first planar slot oriented at a selected angle and at a selected position relative to an anatomic axis of the patient when the engagement surface engages the corresponding surface of the tibial bone, the selected angle and selected position determined during a pre-operative planning stage;
    a patient-specific implantable wedge, the implantable wedge including first and second planar surfaces defining a wedge angle therebetween, the wedge angle custom-selected during pre-operative planning for correcting the patient's anatomy; and
    a patient-specific implantable fixation plate connected with the implantable wedge and having a custom-made surface mating as a negative surface with a corresponding surface of the patient's tibia.

2. The surgical kit of claim 1, wherein the alignment guide defines a plurality of openings receiving bone fasteners for supporting the alignment guide on the tibial bone at a patient specific position and orientation.

3. The surgical kit of claim 1, wherein the alignment guide defines a plurality of guide apertures, the guide apertures oriented and positioned at locations selected during a pre-operative planning stage for attaching a patient-specific implant.

4. The surgical kit of claim 1, wherein the implantable wedge includes a patient-specific curved surface opposite to the wedge angle, the curved surface continuing a contour of the tibial bone between each side of an open-wedge osteotomy.

5. The surgical kit of claim 1, wherein the fixation plate and the implantable wedge comprise a single monolithic implant.

6. The surgical kit of claim 1, wherein the fixation plate and the implantable wedge are removably coupled to one another.

7. The surgical kit of claim 1, wherein the fixation plate and the implantable wedge are removably coupled to one another with a dovetail connection.

8. The surgical kit of claim 1, further comprising a blade.

9. The surgical kit of claim 8, wherein the blade is customized for the patient and has a length corresponding to a pre-operatively determined patient-specific cutting depth.

10. The surgical kit of claim 1, further comprising a second elongated planar slot for guiding a blade, the second planar slot at an angle with the first planar slot for closed osteotomy.

11. The surgical kit of claim 1, further comprising an implantable wedge including a plurality of separate components.

12. A surgical kit comprising:
a patient-specific alignment guide including a three-dimensional engagement surface custom-made by computer imaging to conform as a negative surface to a corresponding surface of a patient's tibial bone, the patient-specific alignment guide defining a first elongated planar slot for guiding a blade, the first planar slot oriented at a selected angle and at a selected position relative to an anatomic axis of the patient when the engagement surface engages the corresponding surface of the tibial bone, the selected angle and selected position determined during a pre-operative planning stage, the patient-specific alignment guide including a central guiding aperture through the planar slot for drilling a guiding hole in the bone; and
a patient-specific implantable wedge, the implantable wedge including an elongated curved central portion and pairs planar surfaces extending radially from the central portion and defining a wedge angle therebetween, the wedge angle selected during pre-operative planning for correcting the patient's anatomy, and wherein the central portion is configured to conform to a shape of the guiding hole drilled through the central guiding aperture of the patient-specific alignment guide.

13. A surgical kit comprising:
a patient-specific implantable wedge for an open-wedge osteotomy, the implantable wedge including first and second planar surfaces forming a patient-specific wedge angle, the implantable wedge including a patient-specific outer surface opposite to the straight edge;
a patient-specific fixation plate, the fixation plate having a patient-specific engagement surface for mating as a negative to a corresponding surface of the patient's tibia and a surface engageable with the implantable wedge; and
a patient-specific alignment guide including a three-dimensional engagement surface custom-made by computer imaging to conform as a negative surface to a corresponding surface of a patient's tibial bone, the patient-specific alignment guide defining an elongated planar slot for guiding a blade, the planar slot oriented at a selected angle and at a selected position relative to an anatomic axis of the patient when the engagement surface engages the corresponding surface of the tibial bone, the selected angle and selected position determined during a pre-operative planning stage.

14. The surgical kit of claim 13, wherein the patient-specific alignment guide defines apertures at patient-specific orientations and positions for guiding bone fasteners for the fixation plate.

15. The surgical kit of claim 13, wherein the implantable wedge and the fixation plate comprise a single monolithically formed component.

16. The surgical kit of claim 13, wherein the implantable wedge and the fixation plate are removably connected.

17. The surgical kit of claim 13, wherein the implantable wedge and the fixation plate are removably connected with a dovetail connection.

18. The surgical kit of claim 13, further comprising a blade with depth control.

19. The surgical kit of claim 13, wherein the implantable wedge includes a plurality of separate components.

20. A surgical kit comprising:
a patient-specific alignment guide including a three-dimensional engagement surface custom-made by computer imaging to conform as a negative surface to a corresponding surface of a patient's tibial bone, the patient-specific alignment guide defining an elongated planar slot for guiding a blade, the planar slot oriented at a preoperatively selected angle and position relative to an anatomic axis of the patient, and
a patient-specific implantable fixation plate having a patient-specific surface mating as a negative surface to a corresponding surface of the patient's tibial bone, and wherein the alignment guide defines a plurality of guide apertures oriented and positioned at locations preoperatively selected for attaching the patient-specific fixation plate to the patient's tibial bone.

* * * * *

UNITED STATES PATENT AND TRADEMARK OFFICE
Certificate

Patent No. 8,241,293 B2                                                                            Patented: August 14, 2012

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kevin T. Stone, Winona Lake, IN (US); Robert Metzger, Wakarusa, IN (US); and Louis J. Keppler, Valley City, OH (US).

Signed and Sealed this Thirtieth Day of September 2014.

*DAVID J. ISABELLA*
*Supervisory Patent Examiner*
*Art Unit 3774*
*Technology Center 3700*